(12) United States Patent
McDermott

(10) Patent No.: US 7,273,715 B2
(45) Date of Patent: *Sep. 25, 2007

(54) METHODS AND COMPOSITIONS FOR IDENTIFYING THERAPEUTIC COMPOUNDS WITH GS-9005 ESTER HYDROLASE A

(75) Inventor: Martin McDermott, Redwood City, CA (US)

(73) Assignee: Gilead Sciences, Inc., Foster City, CA (US)

(*) Notice: Subject to any disclaimer, the term of this patent is extended or adjusted under 35 U.S.C. 154(b) by 51 days.

This patent is subject to a terminal disclaimer.

(21) Appl. No.: 10/970,388

(22) Filed: Oct. 22, 2004

(65) Prior Publication Data

US 2005/0136396 A1 Jun. 23, 2005

Related U.S. Application Data

(63) Continuation-in-part of application No. PCT/US04/35084, filed on Oct. 22, 2004.

(60) Provisional application No. 60/514,925, filed on Oct. 29, 2003, provisional application No. 60/514,894, filed on Oct. 29, 2003, provisional application No. 60/513,542, filed on Oct. 24, 2003, provisional application No. 60/513,532, filed on Oct. 24, 2003, provisional application No. 60/514,299, filed on Oct. 24, 2003, provisional application No. 60/514,241, filed on Oct. 24, 2003.

(51) Int. Cl.
C12Q 1/34 (2006.01)

(52) U.S. Cl. ......................................................... 435/18

(58) Field of Classification Search .................... None
See application file for complete search history.

(56) References Cited

U.S. PATENT DOCUMENTS

| | | | |
|---|---|---|---|
| 5,413,996 A | 5/1995 | Bodor | |
| 5,670,497 A | 9/1997 | Bold et al. | |
| 5,750,343 A | 5/1998 | Maag et al. | |
| 5,750,493 A | 5/1998 | Sommadossi et al. | |
| 5,874,577 A | 2/1999 | Chen et al. | |
| 5,914,332 A | 6/1999 | Sham et al. | |
| 6,072,053 A | 6/2000 | Vince et al. | |
| 6,312,662 B1 | 11/2001 | Erion et al. | |
| 6,319,946 B1 | 11/2001 | Hale et al. | |
| 6,767,900 B2 | 7/2004 | Ubasawa et al. | |
| 2001/0031773 A1 | 10/2001 | Camden | |
| 2003/0109498 A1 | 6/2003 | Yuasa et al. | |
| 2004/0121316 A1 | 6/2004 | Birkus et al. | |

FOREIGN PATENT DOCUMENTS

| | | |
|---|---|---|
| EP | 0 267 050 A2 | 5/1988 |
| EP | 0 441 192 A2 | 8/1991 |
| EP | 0 465 297 A1 | 1/1992 |
| EP | 0 531 597 A1 | 3/1993 |
| EP | 0 632 048 A1 | 1/1995 |
| EP | 0 786 455 A1 | 7/1997 |
| EP | 0 852 233 A1 | 7/1998 |
| EP | 0 919 562 A1 | 6/1999 |
| EP | 1 295 879 A1 | 3/2003 |
| WO | WO88/06158 | 8/1988 |
| WO | WO91/19721 | 12/1991 |
| WO | WO92/00988 | 1/1992 |
| WO | WO92/18520 | 10/1992 |
| WO | WO93/12123 | 6/1993 |
| WO | WO93/24510 | 12/1993 |
| WO | WO96/14314 | 5/1996 |
| WO | WO96/40156 | 12/1996 |
| WO | WO 1997/15588 A1 | 5/1997 |
| WO | WO98/04569 | 2/1998 |
| WO | WO98/11906 | 3/1998 |
| WO | WO99/62921 | 12/1999 |
| WO | WO 00/04033 | 1/2000 |
| WO | WO 00/52015 | 9/2000 |
| WO | WO 01/13957 A2 | 3/2001 |
| WO | WO 01/13957 A3 | 3/2001 |
| WO | WO 01/17982 A1 | 3/2001 |
| WO | WO 01/19320 A2 | 3/2001 |
| WO | WO 01/19320 A3 | 3/2001 |
| WO | WO 01/39724 A2 | 6/2001 |
| WO | WO 01/46204 A1 | 6/2001 |
| WO | WO 01/64693 A1 | 9/2001 |
| WO | WO 01/39724 A3 | 10/2001 |
| WO | WO 01/96329 A1 | 12/2001 |

(Continued)

OTHER PUBLICATIONS

Abdel-Meguid et al., "Inhibition of Human Immunodeficiency Virus-1 Protease by a $C_2$-Symmetric Phosphinate. Synthesis and Crystallographic Analysis", *Biochemistry*, 32(31):7972-7980 (1993).

Allen et al., "CI-1040 (PDI84352), a Targeted Signal Transduction Inhibitor of MEK (MAPKK)", *Seminars in Oncology*, 30(5, Suppl. 16):105-116 (2003).

Andrade et al., "HIV-Related Drug Metabolism and Cytochrome P450 Enzymes" *AIDS Clinical Care*, 12(11):91-95 (2000).

Bantia et al., "Purine Nucleoside Phosphorylase Inhibitor BCX-1777 (Immucillin-H)—A Novel Potent and Orally Active Immunosuppressive Agent", *International Immunopharmacology*, 1:1199-1210 (2001).

(Continued)

*Primary Examiner*—Ralph Gitomer
*Assistant Examiner*—Bin Shen
(74) *Attorney, Agent, or Firm*—Arnold & Porter, LLP

(57) ABSTRACT

By the present invention, enzymes responsible for prodrug activation are identified and utilized for the identification of candidate compounds as prodrugs. The present invention includes methods for identifying a candidate compound as a suitable prodrug as well as methods of screening candidate compounds for suitability as therapeutic agents.

17 Claims, 4 Drawing Sheets

FOREIGN PATENT DOCUMENTS

| WO | WO 01/96354 A1 | 12/2001 |
|---|---|---|
| WO | WO 02/03997 A1 | 1/2002 |
| WO | WO 02/06292 A1 | 1/2002 |
| WO | WO 02/08241 A2 | 1/2002 |
| WO | WO 02/14344 A2 | 2/2002 |
| WO | WO 02/057425 A2 | 7/2002 |
| WO | WO 02/100415 A2 | 12/2002 |
| WO | WO 02/100415 A3 | 12/2002 |
| WO | WO 02/103008 A2 | 12/2002 |
| WO | WO 03/028737 A1 | 4/2003 |
| WO | WO 03/050129 A1 | 6/2003 |
| WO | WO 03/059255 A2 | 7/2003 |
| WO | WO 03/064383 A1 | 8/2003 |
| WO | WO 03/066005 A2 | 8/2003 |
| WO | WO 03/080078 A1 | 10/2003 |
| WO | WO 02/103008 A3 | 11/2003 |
| WO | WO 03/090690 A2 | 11/2003 |
| WO | WO 04/096234 A2 | 11/2004 |
| WO | WO 2004/096818 A2 | 11/2004 |
| WO | WO 2004/096818 A3 | 11/2004 |
| WO | WO 05/011709 A1 | 2/2005 |

OTHER PUBLICATIONS

Beauchamp, et al., "Guanine, Pyrazolo[3,4-d]pyrimidine, and Triazolo[4,5-d]pyrimidine(8-Azaguanine) Phosphonate Acyclic Derivatives as Inhibitors of Purine Nucleoside Phosphorylase", *Journal of Medicinal Chemistry*, 39:949-956 (1996).

Borhani et al., "A-420983: A Potent, Orally Active Inhibitor of lck with Efficacy in a Model of Transplant Rejection", *Bioorganic & Medicinal Chemistry Letters*, 14:2613-2616 (2004).

Bzowska et al., "Purine Nucleoside Phosphorylases: Properties, Functions, and Clinical Aspects", *Pharmacology & Therapeutics*, 88:349-425 (2000).

Chapman et al., "Practical Synthesis, Separation, and Stereochemical Assignment of the PMPA Pro-Drug GS-7340", *Nucleosides, Nucleotides & Nucleic Acids*, 20(4-7):621-628 (2001).

Charvet et al., "Inhibition of Human Immunodeficiency Virus Type I Replication by Phosphonoformate- and Phosphonoacetate-2',3'-Dideoxy-3'-thiacytidine Conjugates", *Journal of Medicinal Chemistry*, 37(14):2216-2223 (1994).

Clark et al., Abstract, "Mycophenolic Acid Analogues as Potential Agents Against West Nile Virus Infection", Institute for Antiviral Research, Utah State University.

Conklyn et al., "The JAK3 Inhibitor CP-690550 Selectively Reduces NK and CD8+ Cell Numbers in Cynomolgus Monkey Blood Following Chronic Oral Dosing", *Journal of Leukocyte Biology*, 76:1-8 (2004).

DeClercq, "Chemotherapy of Human Immunodeficiency Virus (HIV) Infection: Anti-HIV Agents Target at Early Stages in the Virus Replicative Cycle", *Biomedicine and Pharmacotherapy*, 50(5):207-215 (1996).

DeClercq, "Highlights in the Development of New Antiviral Agents", *Mini Reviews in Medicinal Chemistry*, 2(2):163-175 (2002).

DeClercq, "New Developments in Anti-HIV Chemotherapy", *Current Medicinal Chemistry*, 8(13):1543-1572 (2001).

Dvořáková et al., "Synthesis of 2'-Aminomethyl Derivatives of N-(2-(Phosphonomethoxy)ethyl) Nucleotide Analogues as Potential Antiviral Agents", *J. Med. Chem.*, 39(17):3263-3268 (1996).

Eisenberg et al., "Metabolism of GS-7340, a Novel Phenyl Monophosphoramidate Intracellular Prodrug of PMPA, in Blood", *Nucleosides, Nucleotides & Nucleic Acids*, 20(4-7):1091-1098 (2001).

Evans et al., "Exploring Structure-Activity Relationships of Transition State Analogues of Human Purine Nucleoside Phosphorylase", *J. Med. Chem.*, 46(15):3412-3423 (2003).

Gobec et al., Phosphonate Inhibitors of Antigen 85C, a Crucial Enzyme Involved in the Biosynthesis of the *Mycobacterium tuberculosis* Cell Wall, *Bioorganic and Medicinal Chemistry Letters*, 14:3559-3562 (2004).

Gorin et al., "A Novel Esterification Procedure Applied to Synthesis of Biologically Active Esters of Foscarnet", *Tetrahedron Letters*, 38(16):2791-2794 (1997).

Gumina et al., "Advances in antiviral agents for Hepatitis B Virus", *Antiviral Chemistry & Chemotherapy*, 12(Suppl. 1):93-117 (2001).

Hakimelahi et al., "Design, Synthesis, and Structure-Activity Relationship of Novel Dinucleotide Analogs as Agents Against Herpes and Human Immunodeficiency Viruses", *Journal of Medicinal Chemistry*, 38(23);4648-4659 (1995).

Hammon et al., "Alkylglycerol Prodrugs of Phosphonoformate are Potent In Vitro Inhibitors of Nucleoside-Resistant Human Immunodeficiency Virus Type 1 and Select for Resistance Mutations that Suppress Zidovudine Resistance", *Antimicrobial Agents and Chemotherapy*, 45(6):1621-1628 (2001).

Hegedus et al., "Synthesis of 4'-Methyl and 4'-Cyano Carbocyclic 2',3'-Didehydro Nucleoside Analogues via 1,4-Addition to Substituted Cyclopentenones", *J. Org. Chem.*, 69(24):8492-8495 (2004).

Herczegh et al., "Osteoadsorptive Bisphosphonate Derivatives of Fluoroquinolone Antibacterials", *J. Med. Chem.*, 45:2338-2341 (2002).

Hirabayashi et al., "Bone-Specific Drug Delivery Systems: Approaches via Chemical Modification of Bone-Seeking Agents", *Clinical Pharmacokinetics*, 42(15):1319-1330 (2003).

Holý et al., "Synthesis of N-(2-Phosphonylmethoxyethyl Derivatives of Heterocyclic Bases", *Collect. Czech. Chem. Commun.*, 54:2190-2210 (1989).

International Search Report for International Application No. PCT/EP2003/012423, mailed Feb. 11, 2005.

International Search Report for International Application No. PCT/US2004/042991, mailed Jun. 6, 2005.

Jain et al., "Characterization of Pharmacological Efficacy of VX-148, a New, Potent Immunosuppressive Inosine 5'-Monophosphate Dehydrogenase Inhibitor", *Journal of Pharmacology and Experimental Therapeutics*, 302(3):1272-1277 (2002).

Karpenko et al., "Synthesis and Antiherpetic Activity of Acyclovir Phosphonates", *Nucleosides, Nucleotides & Nucleic Acids*, 22(3):319-328 (2003).

Kato et al., "Enantio- and Diastereoselective Synthesis of 4'-α-Substituted Carbocyclic Nucleosides", *Tetrahedron: Asymmetry*, 9:911-914 (1998).

Kato et al., "Stereoselective Synthesis of 4' -β-alkylcarbovir Derivatives Based on an Asymmetric Synthesis or Chemo-Enzymatic Procedure", *Chemical & Pharmaceutical Bulletin*, 47(9):1256-1264 (1999).

Kilpatrick et al., "Intravenous and Oral Pharmacokinetic Study of BCX-1777, a Novel Purine Nucleoside Phosphorylase Transition-State Inhibitor, In vivo Effects on Blood 2'-Deoxyguanosine in Primates", *International Immunopharmacology*, 3:541-548 (2003).

Kim et al., "Regiospecific and Highly Stereoselective Electrophilic Addition to Furanoid Glycals: Synthesis of Phosphonate Nucleotide Analogues with Potent Activity Against HIV", *J. Org. Chem.*, 56(8):2642-2647 (1991).

Kinsky et al., "Inhibition of Cell Proliferation by Putative Metabolites and Non-Degradable Analogs of Methotrexate-γ-Dimyristoylphosphatidylethanolamine", *Biochimica et Biphysica Acta*, 917(2):211-218 (1987).

Kinsky et al., "Effect of Liposomes Sentitized with Methotrexate-γ-Dimyristoylphosphatidylethanolamine on Cells that are Resistant to Methotrexate", *Biochimica et Biophysica Acta*, 885:129-135 (1986).

Kinsky et al., "Circumvention of the Methotrexate Transport System by Methotrexate-Phosphatidylethanolamine Derivatives Effect of Fatty Acid Chain Length", *Biochimica et Biophysica Acta*, 921:96-103 (1987).

Ko et al., "Efficient Synthesis of Novel Carbocyclic Nucleosides via Sequential Claisen Rearrangement and Ring-Closing Metathesis", *Tetrahedron Letters*, 43:6399-6402 (2002).

Kofoed et al., "Regiosomers of 2',3'-Dideoxynucleosides Related to 2-(Phosphonylmethoxy)ethyl Nucleosides", *Bulletin de la Societe Chimique de France*, 134:59-65 (1997).

Kraus, "New Phosphonate Analogues of 3'-thia-2',3'-Dideoxycytidine (BCH-189) Synthesis and Anti-HIV Evaluation", *Nucleosides & Nucleotides*, 12(2):157-162 (1993).

Leff et al., "The Antidiabetic PPARγ Ligands: An Update on Compounds in Development", Curr. Med. Chem.-Imun., Endoc. & Metab. Agents 2(1):33-47 (2002).

Lewandowicz et al., "Achieving the Ultimate Physiological Goal in Transition State Analogue Inhibitors for Purine Nucleoside Phosphorylase", *The Journal of Biological Chemistry*, 278(34):31465-31468 (2003).

McGuigan et al., "Synthesis and Anti-HIV Activity of Some Novel Chain-Extended Phosphoramidate Derivatives of d4T (Stavudine): Esterase Hydrolysis as a Rapid Predictive Test for Antiviral Potency", *Antiviral Chemistry & Chemotherapy*, 9:109-115 (1998)

McGuigan et al., Synthesis, Anti-Human Immunodeficiency Virus Activity and Esterase Lability of Some Novel Carboxylic Ester-Modified Phosphoramidate Derivatives of Stavudine (d4T), *Antiviral Chemistry & Chemotherapy*, 9:473-479 (1998).

Mendes et al., "Synthesis, Stability and In Vitro Dermal Evaluation of Aminocarbonyloxymethyl Esters as Prodrugs of Carboxylic Acid Agents", *Bioorganic & Medicinal Chemistry*, 10(3):809-816 (2002).

Menéndez-Arias, "Targeting HIV: Antiretroviral Therapy and Development of Drug Resistance", *TRENDS in Pharmacological Sciences*, 23(8):381-388 (2002).

Ono-Nita et al., "Novel Nucleoside Analogue MCC-478 (LY582563) Is Effective Against Wild-Type or Lamivudine-Resistant Hepatitis B Virus", *Antimicrobial Agents and Chemotherapy*, 46(8):2602-2605 (2002).

Pankiewicz et al., "Novel Mycophenolic Adenine Bis(phosphonate) Analogues As Potential Differentiation Agents Against Human Leukemia", *J. Med. Chem.*, 45(3):703-712 (2002).

Parang et al., "Novel Approaches for Designing 5'-O-Ester Prodrugs of 3'-Azido-2', 3'-Dideoxythymidine (AZT)", *Current Medicinal Chemistry*, 7(10):995-1039 (2000).

Pokrovskii et al, "Comparative Analysis of HIV-1 Resistance to AZT and AZT H-Phosphonate in a Cell Culture", Doklady Biochemistry and Biophysics, 384:152-154 (2002).

Prashad et al., "An Efficient and Large-Scale Enantioselective Synthesis of PNP405: A Purine Nucleoside Phosphorylase Inhibitor", J. Org. Chem., 67(19):6612-6617 (2002).

Ray et al., "Role of Purine Nucleoside Phosphorylase in Interactions between 2', 3'-Dideoxyinosine and Allopurinal, Ganciclovir, or Tenofovir", Antimicrobial Agents and Chemotherapy, 48(4):1089-1095 (2004).

Roberts, "Development of the Route to the New Anti-AIDS drug Abacavir: A highlight of Academic/Industry Liaison", *IDrugs*, 1(8):896-899 (1998).

Rosowsky et al., "Methotrexate Analogues—27", *Biochemical Pharmacology*, 35(19):3327-3333 (1986).

Rosowsky et al., "Methotrexate Analogues, 32, Chain Extension, α-Carboxyl Deletion, and γ-Carboxyl Replacement by Sulfonate and Phosphonate: Effect on Enzyme Binding and Cell-Growth Inhibition", *J. Med. Chem.*, 31(7):1326-1331 (1988).

Saboulard et al., "Characterization of the Activation Pathway of Phosphoramidate Triester Prodrugs of Stavudine and Zidovudine", *Molecular Pharmacology*, 56:693-704 (1999).

Sauber et al., "A New Esterase for the Cleavage of Pivalic Acid-Containing Prodrug Esters of Cephalosporins", *Enzyme and Microbial Technology*, 19:15-19 (1996).

Schultz, "Prodrugs of Biologically Active Phosphate Esters", *Bioorganic & Medicinal Chemistry*, 11:885-898 (2003).

Sekiya et al., "2-Amino-6-Arylthio-9-[2-(Phosphonomethoxy) Ethyl) Purine Bis(2,2,2-Trifluoroethyl) Esters as Novel HBV-Specific Antiviral Reagents", *Journal of Medicinal Chemistry*, 45(14):3138-3142 (2002).

Shi et al., "*Plasmodium falciparum* Purine Nucleoside Phosphorylase", *The Journal of Biological Chemistry*, 279(18):18103-18106 (2004).

Sintchak et al., "The Structure of Inosine 5'-Monophosphate Dehydrogenase and the Design of Novel Inhibitors" *Immunopharmachology*, 47:163-184 (2000).

Srinivas et al., "Metabolism and In Vitro Antiretroviral Activities of Bis(Pivaloyloxymethyl) Prodrugs of Acyclic Nucleoside Phosphonates", *Antimicrobial Agents and Chemotherapy*, 37(10):2247-2250 (1993).

Sturtz et al., "Sur une nouvelle Approche de Pharmacomodulation du Methotrexate: Synthese D'analogues Gem-Diphosphoniques D'amethopterine et de la N-10 Deaza Amethopterine", *Medicinal Chemistry*, C. R. Acad. Sci. Paris, 10(2):739-742 (1990).

Sturtz et al., "Analogues Phosphonoglutamiques D'amethopterine (Methotrexate)", *Eur. J. Med. Chem—Chim. Ther.*, 19(3):267-273 (1984).

Sturtz et al., "Synthesis of Gem-Bisphosphonic Methotrexate Conjugates and Their Biological Response Towards Walker's Osteosarcoma", *Eur. J. Med. Chem.*, 28:899-903 (1993).

Sturtz et al., "A Study of the Delivery-Targeting Concept Applied to Antineoplasic Drugs Active on Human Osteosarcoma, I. Synthesis and Biological Activity in Nude Mice Carrying Human Osteosarcoma Xenografts of Gem-Bisphosphonic Methotrexate Analogues", *Eur. J. Med. Chem.*, 27(8):825-833 (1992).

Vielhaber, "Bericht vom 3rd International Workshop on Salvage Therapy for HIV-Infection", *Deutsche Aids-Hilfe e.V. Fax Report zu HIV und AIDS*, Seite 4 (2000).

Waegell et al., "A420983, a Novel, Small Molecule Inhibitor of LCK Prevents Allograft Rejection", *Transplantation Proceedings*, 34:1411-1417 (2002).

Wróblewski et al., Synthesis of (1R,2S)- and (1S,2S)-3-(4-Carbamoyl-1,2,3-triazol-1-yl)-1,2-Dihydroxypropylphosphonates, *Tetrahedron: Asymmetry*, 15:1457-1464 (2004).

International Search Report for International Application No. PCT/US2004/035083.

Ballatore, C., et al., "Synthesis and Evaluation of Novel Amidate Prodrugs of PMEA and PMPA", *Bioorganic & Medicinal Chemistry Letters*, Oxford, GB, vol. 11, 2001, pp. 1053-1056.

International Search Report for International Application No. PCT/US2004/035084.

International Search Report for International Application No. PCT/US2004/035085.

Siddiqui, A. Q., et al., "Design and Synthesis of Lipophilic Phosphoramidate d4T-MP Prodrugs Expressing High Potency Against HIV in Cell Culture: Structural Determinants for in Vitro Activity and QSAR", *Journal of Medicinal Chemistry*, American Chemical Society, Washington, DC, vol. 42, No. 20, 1999, pp. 4122-4128.

Tan, Fulong, et al., "Sequencing and Cloning of Human Prolylcarboxypeptidase (Angiotensinase C): Similarity to Both Serine Carboxypeptidase and Prolylendopeptidase Families", *Journal of Biological Chemistry*, American Society of Biological Chemists, Baltimore, MD, vol. 268, No. 22, 1993, pp. 16631-16638.

Valette, G. et al., "Decomposition Pathways and in Vitro HIV Inhibitory Effects of IsoddA Pronucleotides: Toward a Rational Approach for Intracellular Delivery of Nucleoside 5'-Monophosphates", *Journal of Medicinal Chemistry*, American Chemical Society, Washington, DC, vol. 39, No. 10, 1996, pp. 1981-1990.

Identification of Serine Hydrolases in 9005 Hydrolase A Fraction Labeled with AX4870 Probe Lysosomal Pro-X carboxypeptidase precursor (EC 3.4.16.2) (PCP_HUMAN)

TIPGAENQPVIAIGGS*YGGMLAAWFR.-

METHODS AND COMPOSITIONS FOR IDENTIFYING THERAPEUTIC COMPOUNDS WITH GS-9005 ESTER HYDROLASE A

The present application claims the benefit under 35 U.S.C. § 119(e) of U.S. Provisional Application No. 60/514,241, filed Oct. 24, 2003, U.S. Provisional Application No. 60/514,299, filed Oct. 24, 2003, U.S. Provisional Application No. 60/513,532, filed Oct. 24, 2003, U.S. Provisional Application No. 60/513,542, filed Oct. 24, 2003, U.S. Provisional Application No. 60/514,894, filed Oct. 29, 2003, and U.S. Provisional Application No. 60/514,925, filed Oct. 29, 2003. Each of the aforementioned applications for which the benefit is claimed under 35 U.S.C. § 119(e) is herein incorporated by reference in its entirety. The present application is also a continuation of, PCT/US04/35084 and claims the benefit under 35 U.S.C. § 120 of, PCT application entitled "Methods and Compositions for Identifying Therapeutic Compounds", filed Oct. 22, 2004, which PCT application is herein incorporated by reference in its entirety.

FIELD OF THE INVENTION

By the present invention, enzymes responsible for prodrug activation are identified and utilized for the identification of candidate compounds as prodrugs. The present invention includes methods for identifying a candidate compound as a suitable prodrug as well as methods of screening candidate compounds for suitability as therapeutic agents.

BACKGROUND

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the drug with its intracellular target, while minimizing intercellular redistribution of the drug, e.g., to neighboring cells, is often difficult or inefficient. Accordingly, a major goal has been to develop methods and compositions for specifically targeting agents to cells and tissues. Benefits of such treatment include avoiding the general physiological effects of inappropriate delivery of such agents to other cells and tissues, such as uninfected cells.

Intracellular targeting may be achieved by methods and compositions that allow accumulation or retention of biologically active agents inside cells.

Assay methods capable of determining the presence, absence or amounts of an infectious agent or presence or absence of a medical condition are of practical utility in the search for inhibitors of such an agent or condition.

There is a need for therapeutic agents, e.g., prodrugs, having desired pharmacokinetic properties, including enhanced activity, improved oral bioavailability, greater potency and extended effective half-life in vivo. Identified prodrugs will preferably have fewer side effects, less complicated dosing schedules, and be orally active. Such prodrugs may be useful to limit the establishment and progression of a medical condition as well as in diagnostic assays for a medical condition. As such, a need exists for enzymes that facilitate the identification of such prodrugs.

There is consensus that the bioactivation of phosphoramidate prodrugs such as nucleotide amidate triesters may follow a general scheme (Valette et al., J. Med. Chem., 39: 1981-1991 (1996); McGuigan et al., Antivir. Chem. Chemotheraphy, 9: 109-115 (1998), McGuigan et al., Antivir. Chem. Chemotheraphy, 9:473-479 (1998); Saboulard et al., Mol. Pharmacol., 56: 693-704 (1999); Siddiqui et al., J. Med. Chem., 42:4122-4128 (1999)). See FIG. 1. Step A is the hydrolysis of the amino acid-like carboxylic ester. A nucleophilic attack by the carboxylic acid of the phosphorous (Step B) is believed to initiate the formation of a 5-membered cyclic intermediate, which intermediate is quickly hydrolyzed to the monoamidate diester (referred to as the amino acid nucleoside monophosphate, AAM, Metabolite X). AAM compounds such as Metabolite X are considered intracellular depot forms, for example of antiviral nucleoside. Various enzymes as well as non-enzymatic catalysis have been implicated in the hydrolysis of the amide bond of AAM compounds resulting in the formation of the nucleotide. The nucleotide is activated by enzymatic phosphorylation to nucleotide di- and tri-phosphates. Ester hydrolase activity might also be hypothesized to apply to prodrug molecules other than phosphoramidates. However, until now identification of the mechanisms and specificities of ester hydrolase cleavage of prodrugs has been constrained by the limited availability of identifiable ester hydrolase enzymes.

SUMMARY OF THE INVENTION

The present invention includes and provides a method for identifying a candidate compound as a suitable prodrug, comprising: (a) providing a candidate compound having an esterified phosphonate group or an esterified carboxyl group; (b) contacting the candidate compound with an extract that comprises GS-9005 ester hydrolase A to produce one or more metabolite compounds; and (c) identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

The present invention includes and provides a method for identifying a candidate compound as a suitable prodrug, comprising: (a) providing a candidate compound having an esterified phosphonate group or an esterified carboxyl group; (b) contacting the candidate compound with an extract of peripheral blood mononuclear cells that comprises GS-9005 ester hydrolase A to produce one or more metabolite compounds; and (c) identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

The present invention includes and provides a method for identifying a candidate compound as a suitable prodrug, comprising: (a) providing a candidate compound having an esterified phosphonate group; (b) contacting the candidate compound with an extract that comprises GS-9005 ester hydrolase A to produce one or more metabolite compounds; and (c) identifying the candidate compound as a suitable prodrug if at least one of the one or more metabolite compounds has a phosphonic acid group instead of the esterified phosphonate group of the candidate compound.

The present invention includes and provides a method for identifying a candidate compound as a suitable prodrug, comprising: (a) providing a candidate compound having an esterified carboxyl group; (b) contacting the candidate compound with an extract that comprises GS-9005 ester hydrolase A to produce one or more metabolite compounds and (c) identifying the candidate compound as a suitable prodrug if at least one of the one or more metabolite compounds has a carboxylic acid group instead of the esterified carboxyl group of the candidate compound.

The present invention includes and provides a method for identifying a candidate compound as a suitable prodrug, comprising: (a) providing a candidate compound having an esterified phosphonate group or an esterified carboxyl group; (b) contacting the candidate compound with an extract of peripheral blood mononuclear cells that has GS-9005 ester hydrolase A activity, to produce one or more metabolite compounds; and (c) identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

The present invention includes and provides a method of screening candidate compounds for suitability as therapeutic agents, comprising: (a) providing a candidate compound identified as a suitable prodrug by providing a candidate compound having an esterified phosphonate group or an esterified carboxyl group, contacting the candidate compound with an extract that comprises GS-9005 ester hydrolase A to produce one or more metabolite compounds, and identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound; (b) determining the therapeutic activity of the candidate compound; and (c) determining the intracellular persistence of the candidate compound.

The present invention also includes and provides a method for identifying a candidate compound as a suitable prodrug, comprising: (a) providing a candidate compound formed by substituting an esterified phosphonate or an esterified carboxyl group into a prototype compound believed to have therapeutic activity; (b) contacting the candidate compound with an extract of peripheral blood mononuclear cells that comprises GS-9005 ester hydrolase A to produce one or more metabolite compounds; and (c) identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

The present invention also includes and provides a method for identifying a candidate compound as a suitable prodrug comprising: (a) providing a candidate compound having an esterified phosphonate group or an esterified carboxyl group; (b) contacting the candidate compound with an extract that comprises prolylcarboxypeptidase or a fragment thereof to produce one or more metabolite compounds; and (c) identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

The present invention also includes and provides a method for identifying a candidate compound as a suitable prodrug comprising: (a) providing a candidate compound formed by substituting an esterified phosphonate group or an esterified carboxyl group into a prototype compound believed to have therapeutic activity; (b) contacting the candidate compound with an extract of peripheral blood mononuclear cells having carboxylic acid ester hydrolase activity to produce one or more metabolite compounds; and (c) identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

The present invention also includes and provides a method for identifying a candidate compound as a suitable prodrug comprising: (a) providing a candidate compound formed by substituting an esterified phosphonate group or an esterified carboxyl group into a prototype compound believed to have therapeutic activity against human immunodeficiency virus; (b) contacting the candidate compound with an extract of peripheral blood mononuclear cells having carboxylic acid ester hydrolase activity to produce one or more metabolite compounds; and (c) identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

The present invention also includes and provides a method for identifying a candidate compound as a suitable prodrug comprising: (a) providing a candidate compound formed by substituting an esterified phosphonate group or an esterified carboxyl group into a prototype compound believed to have therapeutic activity against inflammation; (b) contacting the candidate compound with an extract of peripheral blood mononuclear cells having carboxylic acid ester hydrolase activity to produce one or more metabolite compounds; and (c) identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

The present invention also includes and provides a method for identifying a candidate compound as a suitable prodrug comprising: (a) providing a candidate compound formed by substituting an esterified phosphonate group or an esterified carboxyl group into a prototype compound believed to have therapeutic activity against cancer; (b) contacting the candidate compound with an extract of peripheral blood mononuclear cells having carboxylic acid ester hydrolase activity to produce one or more metabolite compounds; and (c) identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

DETAILED DESCRIPTION OF THE INVENTION

Definitions

Figure 1:
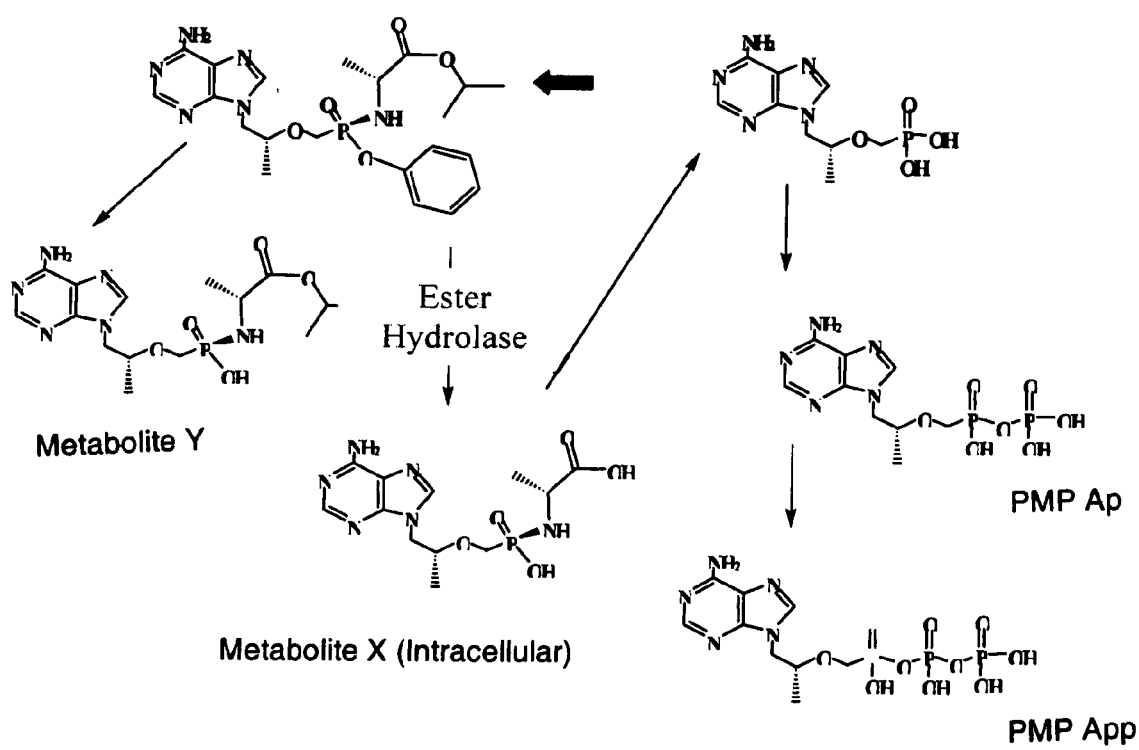
FIG. 1 depicts a scheme for the bioactivation of prodrugs.

As used herein, "cell loading" is the accumulation of a prodrug, prodrug metabolite, or drug molecule inside a cell.

As used herein, an "infectious agent" generally refers to any disease causing organism, including but not limited to, bacteria, viruses, and fungi (including yeast and filamentous fungi).

As used herein, the term "prodrug" refers to any compound that when administered to a biological system generates the drug substance, i.e. active ingredient, as a result of spontaneous chemical reaction(s), enzyme catalyzed chemical reaction(s), photolysis, and/or metabolic chemical reaction(s), i.e., the prodrug forms the drug substance as a prodrug metabolite when administered to a biological system. A prodrug is a covalently modified analog or latent form of a therapeutically-active compound. Prodrugs include compounds that can be oxidized, reduced, aminated, deaminated, esterified, deesterified, alkylated, dealkylated, acylated, deacylated, phosphorylated, dephosphorylated, photolyzed, hydrolyzed, or can have other functional group change or conversion involving forming or breaking chemical bonds on the prodrug. In a preferred embodiment, a prodrug has an esterified phosphonate or an esterified carboxyl group.

As used herein, a "pharmaceutically acceptable prodrug" generally refers to a compound that can be metabolized in a subject, for example hydrolyzed or oxidized, by either enzymatic action or by general acid or base solvolysis, to form an active ingredient. Typical examples of prodrugs of the invention have biologically labile protecting groups on a functional moiety of the compound.

As used herein, a "prototype compound" refers to any candidate compound that is believed to have a therapeutic activity. In general, in the methods of the invention, prototype compounds having known structures and synthesis routes are preferably selected in order to reduce the synthetic burden and development costs.

As used herein, a "subject" is any living organism available to receive treatment for a condition or disease.

A "subject in need of treatment" is any subject, including a human such as a patient, who may benefit from treatment of a disease or condition. Subjects who may benefit from treatment include those who have been diagnosed with a disease or condition, those who are suspected of having a disease or condition, or those who may be susceptible to a disease or condition. Benefits of treatment may include prevention of a disease or condition or amelioration of a disease or condition, including elimination of a disease or condition.

As used herein, samples or subjects that may benefit from treatment include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Samples can be contained in any medium including water and organic solvent/water mixtures. Samples include living organisms such as humans, and man made materials such as cell cultures.

As used herein, a "target enzyme" refers to any enzyme whose specific activity is sought to be enhanced.

As used herein, "therapeutic activity" includes the ability of a compound to induce a response when administered to a subject or tested in vitro. Therapeutic activity includes treatment, which may be prophylactic or ameliorative. Treatment of a disease or condition can include improvement of a disease or condition by any amount, including elimination of a disease or condition. In order to determine the therapeutic activity of a compound may be evaluated can be used. For example, both in vivo and in vitro methods can be used, including for example, clinical evaluation, $EC_{50}$, and $IC_{50}$ assays, and dose response curves.

As used herein, "GS-9005 ester hydrolase A" is also referred to as GS-9005 hydrolase A and 9005 hydrolase A, for example.

Extract Enzymes and Polypeptides of the Present Invention

The present invention includes enzymes or fragments thereof. For example, in an embodiment, the present invention includes GS-9005 hydrolase A and fragments thereof and homologs thereof. In another embodiment, the present invention includes prolylcarboxypeptidase and fragments and homologs thereof. In another embodiment, the present invention includes one or more enzymes and fragments thereof with GS-9005 ester hydrolase A activity. In another embodiment, the present invention includes an enzyme with prolylcarboxypeptidase-like activity.

In a preferred embodiment, the invention includes an extract comprising one or more enzymes of the present invention or fragments or homologs thereof. An extract has typically been extracted, removed, or obtained from any location or source. An extract may be extracted, removed, or obtained by any technique or combination of techniques apparent to the artisan, including those techniques known in the art and those described herein. By way of non-limiting example, an extract may be obtained as described in Example 4.

An extract may comprise any combination of one or more enzymes or fragments thereof and any other components, such as for example, cellular components, buffers or any other component. An extract may be a solution, suspension, emulsion, powder, or any other form apparent to the skilled artisan. In a preferred embodiment, an extract is obtained from human cells. In a highly preferred embodiment, an extract is obtained from human peripheral blood mononuclear cells. An extract may also be prepared synthetically, including for example by recombinant techniques or by peptide synthesis.

In an embodiment, an extract has ester hydrolase activity. In a preferred embodiment, an extract has ester hydrolase activity but has activity in the cleavage of alpha napthyl acetate (ANA). In another preferred embodiment, an extract has ester hydrolase activity on an esterified carboxylate or an esterified phosphonate but has insignificant activity in the cleavage of alpha napthyl acetate (ANA).

In another embodiment, an extract of the present invention is an extract having carboxylic ester hydrolase activity. In a preferred embodiment, an extract having carboxylic ester hydrolase activity is an extract of peripheral blood mononuclear cells (PBMCs). In a preferred embodiment, an extract has carboxylic ester hydrolase activity, but has insiginificant ester hydrolase activity on the cleaveage of alpha naphthyl acetate (ANA). In another preferred embodiment, an extract has carboxylic ester hydrolase activity and is from PMBCs. In yet another embodiment, the extract from PBMCs having carboxylic ester hydrolase activity comprises GS-9005 ester hydrolase A in a cell-free environment.

In a preferred embodiment of the present invention, ester hydrolase activity is measured as described in Example 2B. Varying amounts of extract comprising enzyme activity are incubated with a prodrug substrate. The metabolites that are produced are extracted from each reaction mixture and separated from the parent prodrug substrate using high performance liquid chromatography (HPLC). In an embodiment, one or more metabolite products extracted comprise about 10%, about 20%, about 30%, about 40%, about 50%, about 60%, about 70%, about 80%, about 90%, about 95%, about 97%, about 98%, about 99% of the total metabolites produced Metabolite products are monitored by spectrophotometry. Ester hydrolase activity is expressed as pmoles of cMetabolite plus Metabolite X' produced/minute/volume enzyme sample.

In a preferred embodiment of the present invention, activity in the cleavage of alpha napthyl acetate is measured as described in Example 3. Varying amounts of extract comprising enzyme activity are incubated with ANA. The cleaved alpha napthyl product is detected by spectrophotometry. Activity is expressed as pmoles product produced per minute per volume enzyme sample.

Insignificant activity in the cleavage of alpha napthyl acetate is preferably activity against ANA that is from about 75% less to about 100% less than the ester hydrolase activity against a candidate compound; preferably from about 90% less to about 100% less than the ester hydrolase activity against a candidate compound; or more preferably about 95% less, 96% less, 97% less, 98% less, 99% less, 99.5% less, or about 99.9% less than the ester hydrolase activity against a candidate compound. In a highly preferred embodiment, insignificant activity in the cleavage of alpha napthyl acetate is no detectable activity against ANA.

In an embodiment, an extract comprises GS-9005 ester hydrolase A or a fragment thereof, where the fragment exhibits GS-9005 ester hydrolase A activity. GS-9005 ester hydrolase A activity includes ester hydrolase activity that is specific, namely it is ester hydrolase activity against a candidate compound and insignificant activity in the cleavage of alpha napthyl acetate (ANA). GS-9005 ester hydrolase A activity includes any activity or combination of activities exhibited by GS-9005 ester hydrolase A, such as for example being inhibited by a particular compound or having a particular specific or relative activity against a prodrug substrate. In an embodiment, an extract has GS-9005 ester hydrolase A activity. In another embodiment, an extract comprises prolylcarboxypeptidase, or a fragment or a homolog thereof.

In another embodiment, an extract comprises an enzyme with prolylcarboxypeptidase-like activity. In the context of the present invention, prolylcarboxypeptidase-like activity includes ester hydrolase activity that is specific, namely it is ester hydrolase activity against a candidate compound and insignificant activity in the cleavage of alpha napthyl acetate (ANA). Prolylcarboxypeptidase-like activity includes any activity or combination of activities exhibited by prolylcarboxypeptidase, such as for example being inhibited by a particular compound or having a particular specific or relative activity against a prodrug substrate.

Inhibitors of GS-9005 ester hydrolase A may include any composition that inhibits GS-9005 ester hydrolase A. Preferred inhibitors of GS-9005 hydrolase A include fluorophosphonate/fluorophosphate (diisopropylfluorophosphate (DFP)), isocoumarins such as 3,4 dichloroisocoumarin (3,4-DCI), and peptide carboxyl esters of chloro- and fluoromethyl ketones (AlaAlaProAla-CMK, AlaAlaProVal-CMK, PheAla-FMK). Many inhibitors of GS-9005 hydrolase A may be dissolved in a stock solution, for example where the solution is comprised of the inhibitor in a solvent such as 100% ethanol or aqueous buffer. In an embodiment, inhibitors are dissolved in 100% ethanol. In a further embodiment, inhibition of GS-9005 ester hydrolase A is performed in a buffered MES solution as described in Example 12.

In one embodiment, GS-9005 ester hydrolase A has a molecular weight of about 85 kDa to about 130 kDa, preferably about 90 kDa to about 125 kDa, more preferably about 100 to about 115 kDa on gel filtration.

In another embodiment, GS-9005 hydrolase A has ester hydrolase activity against a candidate compound and insignificant activity in the cleavage of alpha napthyl acetate (ANA).

In an embodiment, GS-9005 ester hydrolase A has an isoelectric point (pI) of about 6.7 to about 7.7, about 6.8 to about 7.6, about 6.9 to about 7.5, or about 7.0 to about 7.4. In another embodiment, GS-9005 hydrolase A has an isoelectric point of about 6.7, about 6.8, about 6.9, about 7.0, about 7.1, about 7.2, about 7.3, about 7.4, about 7.5, about 7.6, or about 7.7. In a preferred embodiment of the present invention, pI is measured by elution of bound protein from a Mono P column using a linear pH gradient.

Structural data for selected exemplary candidate compounds is provided in Table 1.

TABLE 1

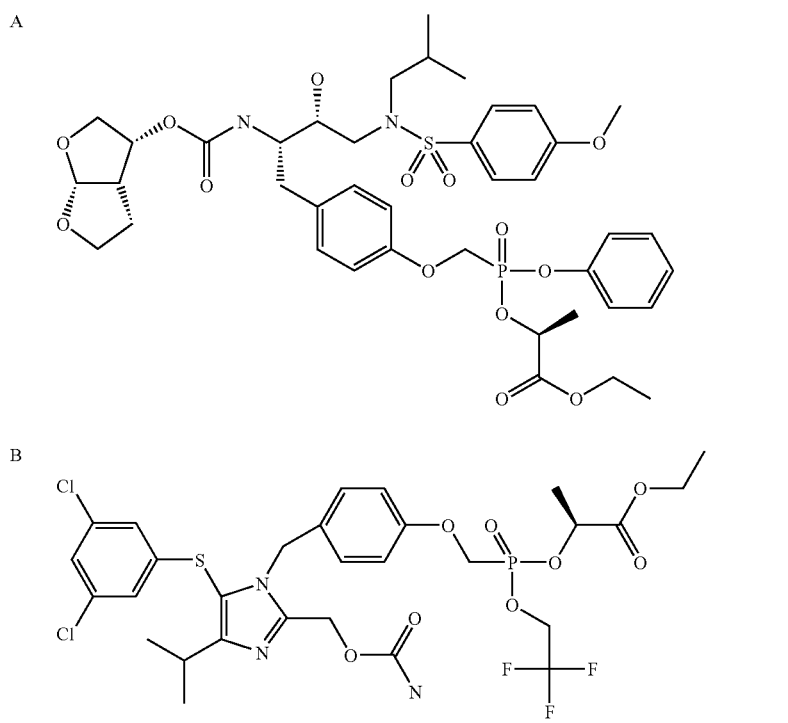

TABLE 1-continued
I
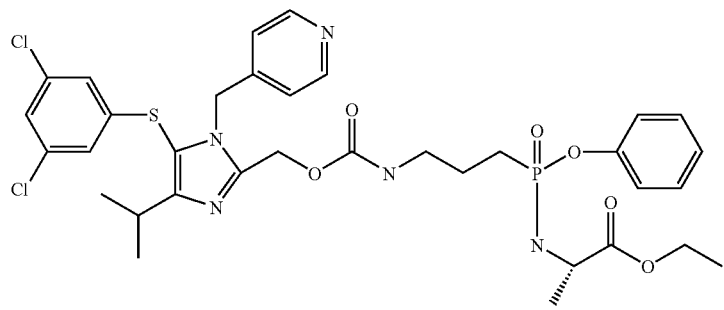
K
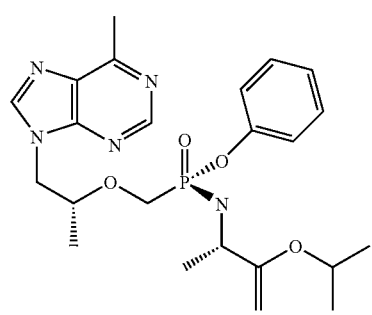
L
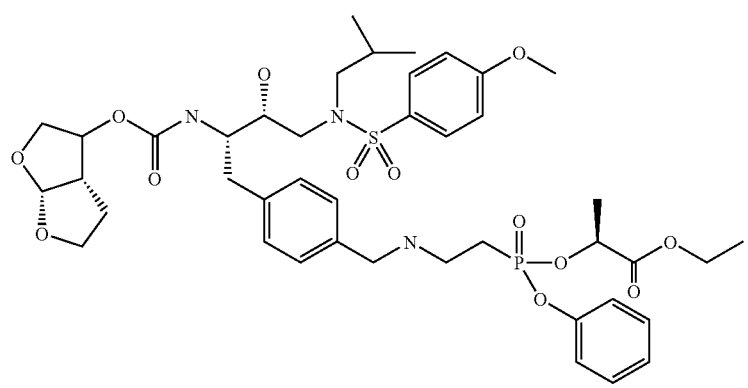
U
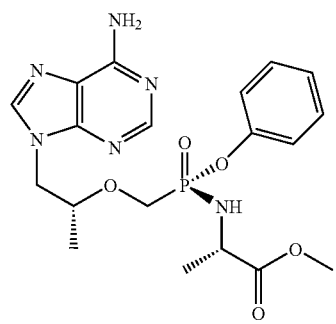

TABLE 1-continued
| | |
|---|---|
| V | 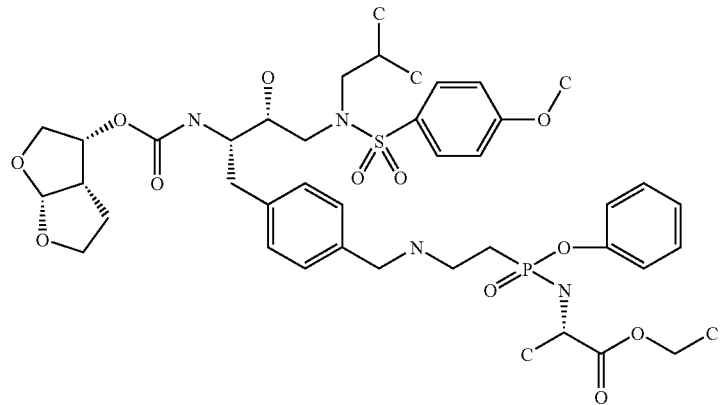 |
| W | 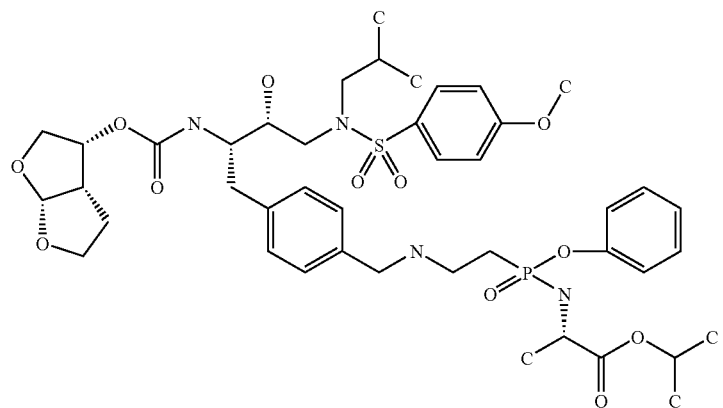 |
| X | 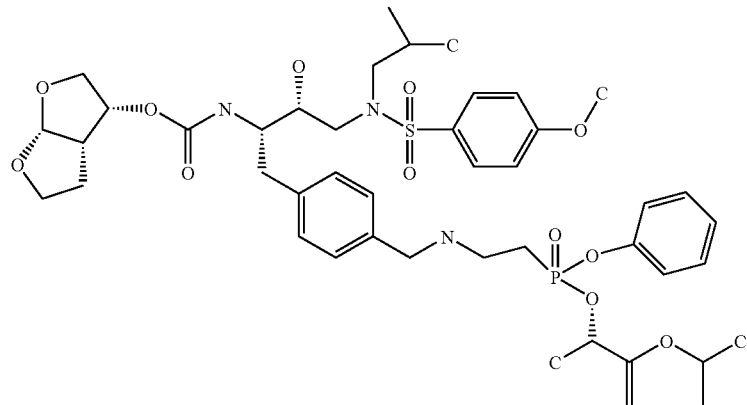 |
| Y | 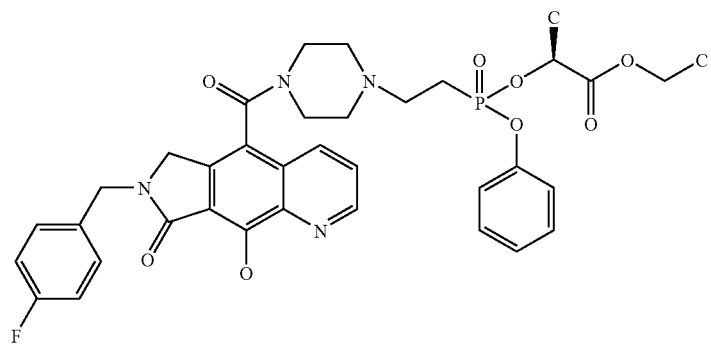 |

TABLE 1-continued
Z
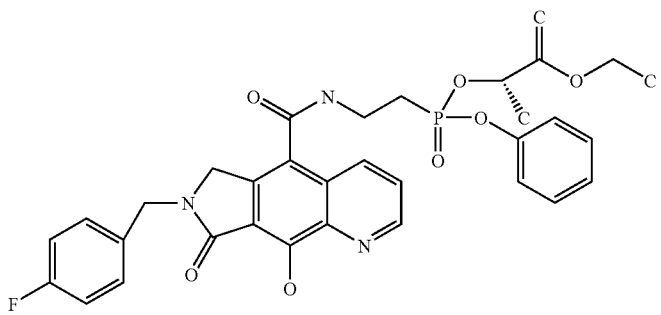
AA
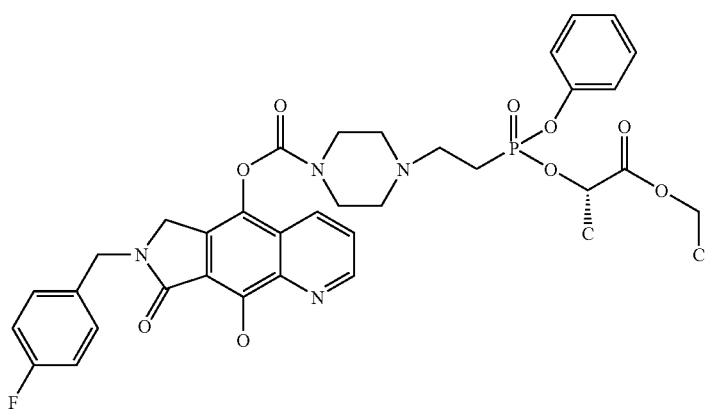
BB
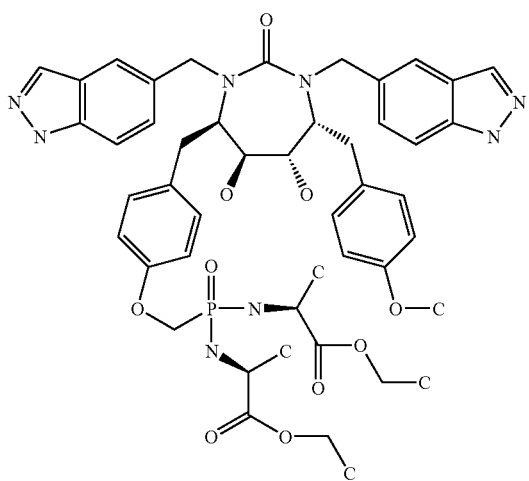

TABLE 1-continued
CC
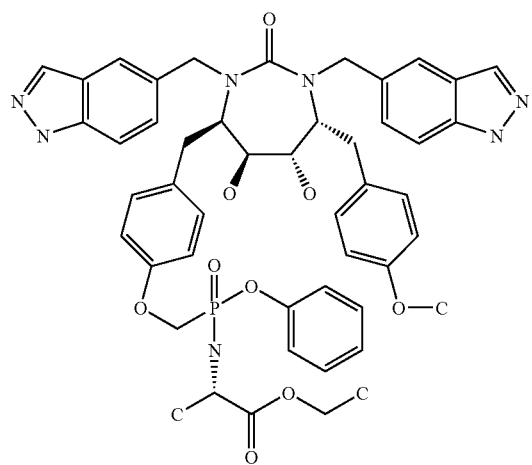
DD
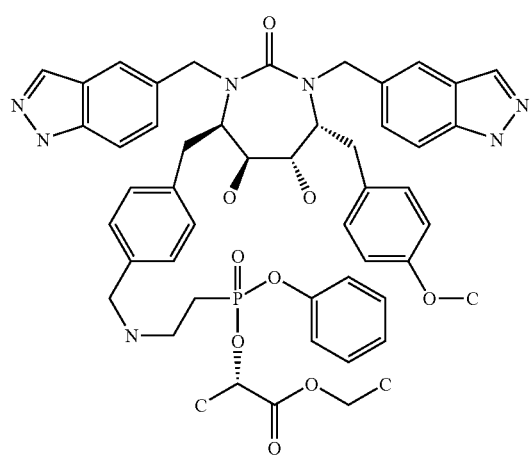
EE
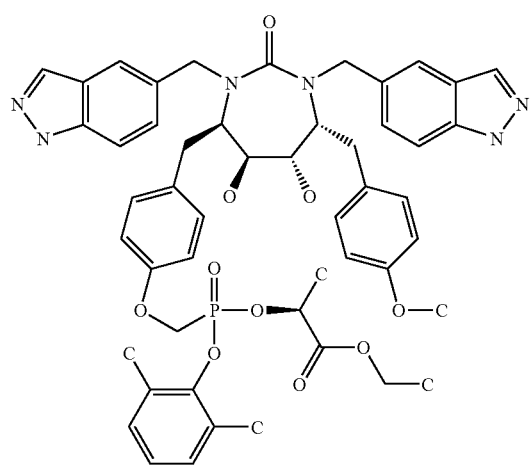

TABLE 1-continued
FF 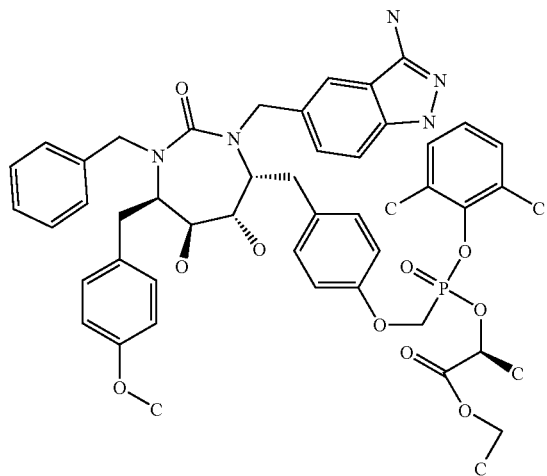
GG 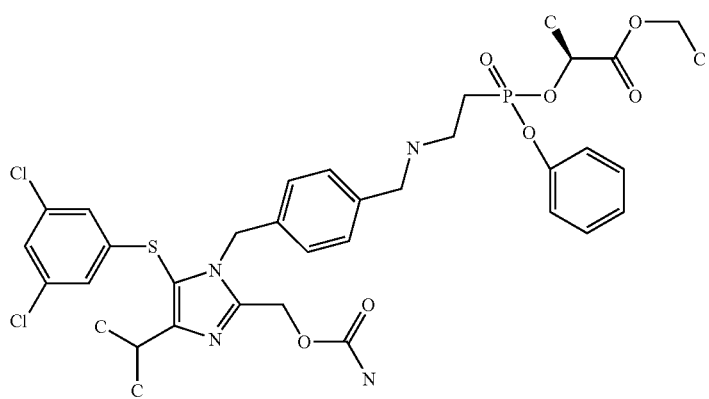
HH 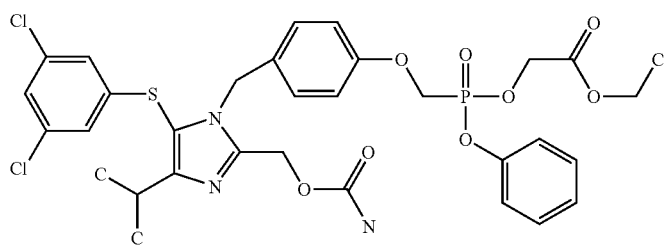
JJ 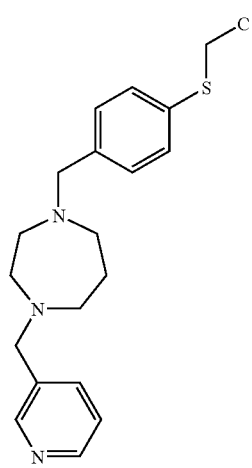

TABLE 1-continued

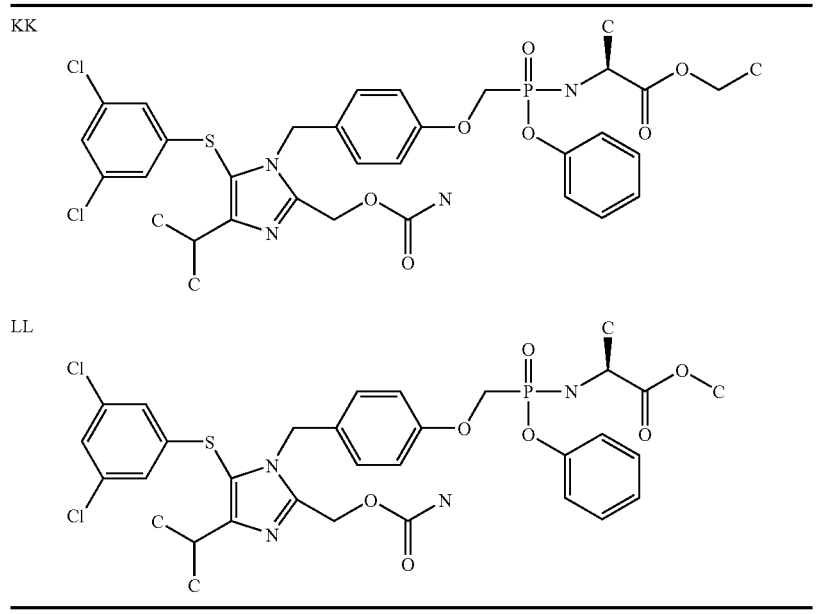

In an embodiment, where all specific activities are estimated based on relative activities, relative to the conversion of Compound A, GS-9005 hydrolase A has an approximately equivalent specific activity against Compound K, Compound U, Compound Z and Compound CC. In an embodiment of the present invention, an approximately equivalent relative or specific activity refers to a relative or specific activity that is less than about 10%, less than about 9%, less than about 8%, less than about 7%, less than about 6%, less than about 5%, less than about 4%, less than about 3%, less than about 2%, or less than about 1%, above or below the value of the largest of the relative or specific activities in any comparison. In an embodiment of the present invention, a relative or specific activity against one compound that is greater than the relative or specific activity against another compound includes a relative or specific activity that is at least about 20% more, at least about 30% more, at least about 40% more, at least about 50% more, at least about 60% more, at least about 70% more, at least about 80% more, at least about 90% more, at least about 100% more, at least about 200% more, at least about 300% more, at least about 500% more, at least about 700% more, at least about 1000% more, at least about 1500% more, at least about 2000% more, at least about 5000% more, or at least about 10,000% more than its relative or specific activity against another candidate compound.

In an embodiment, where all specific activities are estimated based on relative activities, relative to the conversion of Compound A, GS-9005 hydrolase A has an approximately equivalent specific activity against Compound BB and Compound LL.

In an embodiment, where all specific activities are estimated based on relative activities, relative to the conversion of Compound A, GS-9005 hydrolase A has a specific activity against Compound GG greater than its specific activity against Compound DD.

In an embodiment, where all specific activities are estimated based on relative activities, relative to the conversion of Compound A, GS-9005 hydrolase A has a specific activity against Compound Y greater than its specific activity against Compound B.

In an embodiment, where all specific activities are estimated based on relative activities, relative to the conversion of Compound A, GS-9005 hydrolase A has a specific activity against Compound A greater than its specific activity against Compound L.

In an embodiment, where all specific activities are estimated based on relative activities, relative to the conversion of Compound A, GS-9005 hydrolase A has a specific activity against Compound X greater than its specific activity against Compound V.

In an embodiment, where all specific activities are estimated based on relative activities, relative to the conversion of Compound A, GS-9005 hydrolase A has a specific activity against Compound JJ greater than its specific activity against Compound AA.

In an embodiment, where all specific activities are estimated based on relative activities, relative to the conversion of Compound A, GS-9005 hydrolase A has a specific activity against Compound KK greater than its specific activity against Compound FF.

In an embodiment, where all specific activities are estimated based on relative activities, relative to the conversion of Compound A, GS-9005 hydrolase A has a specific activity against Compound EE greater than its specific activity against Compound W.

In an embodiment, where all specific activities are estimated based on relative activities, relative to the conversion of Compound A, GS-9005 hydrolase A has a specific activity against Compound HH greater than its specific activity against Compound I.

In an embodiment, where all specific activities are estimated based on relative activities, relative to the conversion of Compound A, GS-9005 hydrolase A has at least one specific activity, at least 2 specific activities, at least 3 specific activities, at least 4 specific activities, at least 5 specific activities, at least 6 specific activities, at least 7 specific activities, at least 8 specific activities, at least 9 specific activities, or preferably 10 specific activities selected from the group consisting of (1) an approximately equivalent specific activity against Compound K, Compound U, Compound Z and Compound CC; (2) an approximately equivalent specific activity against Compound BB and Compound LL; (3) a specific activity against Compound GG greater than its specific activity against Compound DD; (4) a specific activity against Compound Y greater than its specific activity against Compound B; (5) a specific activity against Compound A greater than its specific activity against Compound L; (6) a specific activity against Compound X greater than its specific activity against Compound V; (7) a specific activity against Compound JJ greater than its specific activity against Compound AA; (8) a specific activity against Compound KK greater than its specific activity against Compound FF; (9) a specific activity against Compound EE greater than its specific activity against Compound W; and (10) a specific activity against Compound HH greater than its specific activity against Compound I.

In an embodiment, GS-9005 hydrolase A is inhibited by 50% by PMSF at a concentration of about 150 to about 250 μm, preferably about 200 μm. In an embodiment, GS-9005 hydrolase A is inhibited by 50% by DFP at a concentration of about 7.5 μm to about 12.5 μm, preferably about 10 μm. In an embodiment, GS-9005 hydrolase A is inhibited by 50% by Cbz-pro-pro-COH at a concentration of about 0.75 μm to about 1.25 μm, preferably about 1.0 μm. In an embodiment, GS-9005 hydrolase A is inhibited by 50% by at least one, at least two, or three compounds selected from the group consisting of PMSF at a concentration of about 150 to about 250 μm, preferably about 200 μm; DFP at a concentration of about 7.5 μm to about 12.5 μm, preferably about 10 μm; Cbz-pro-pro-COH at a concentration of about 0.75 μm to about 1.25 μm, preferably about 1.0 μm. In a preferred embodiment, inhibition is measured by observing the enzymatic production of metabolite by HPLC assay with and without addition of an inhibitor as described in Example 12.

In an embodiment, GS-9005 hydrolase A comprises or consists of SEQ ID NO: 1 or SEQ ID NO: 2 or fragments of either. In an embodiment, GS-9005 hydrolase A comprises or consists of SEQ ID NO: 1 and SEQ ID NO: 2 or fragments of either. In an embodiment, GS-9005 hydrolase A does not comprise or consist of SEQ ID NO: 1 or fragments thereof. In an embodiment, GS-9005 hydrolase A does not comprise or consist of SEQ ID NO: 2 or fragments thereof. In an embodiment, GS-9005 hydrolase A does not comprise or consist of any sequence selected from the group consisting of SEQ ID NO: 1 or SEQ ID NO: 2, and fragments of either.

In an embodiment, GS-9005 hydrolase A has at least one, at least two at least three, at least four, at least five, at least six, or seven characteristics selected from the group consisting of (1) a molecular weight of about 85 kDa to about 130 kDa, preferably about 90 kDa to about 125 kDa, more preferably about 100 to about 115 kDa on gel filtration; (2) ester hydrolase activity against a candidate compound and insignificant activity in the cleavage of alpha napthyl acetate (ANA); (3) an isoelectric point (pI) of about 6.7 to about 7.7, about 6.8 to about 7.6, about 6.9 to about 7.5, about 7.0 to about 7.4, about 6.7, about 6.8, about 6.9, about 7.0, about 7.1, about 7.2, about 7.3, about 7.4, about 7.5, about 7.6, or about 7.7; (4) inhibition by 50% by at least one, at least two, or three compounds selected from the group consisting of PMSF at a concentration of about 150 to about 250 μm, preferably about 200 μm; DFP at a concentration of about 7.5 μm to about 12.5 μm, preferably about 10 μm; Cbz-pro-pro-COH at a concentration of about 0.75 μm to about 1.25 μm, preferably about 1.0 μm; (5) comprising or consisting of a sequence selected from the group consisting of SEQ ID NO: 1, SEQ ID NO: 2 and fragments of either; and (6) where all specific activities are estimated based on relative activities, relative to the conversion of Compound A, GS-9005 hydrolase A has at least one specific activity, at least 2 specific activities, at least 3 specific activities, at least 4 specific activities, at least 5 specific activities, at least 6 specific activities, at least 7 specific activities, at least 8 specific activities, at least 9 specific activities, or preferably 10 specific activities selected from the group consisting of (i) an approximately equivalent specific activity against Compound K, Compound U, Compound Z and Compound CC; (ii) an approximately equivalent specific activity against Compound BB and Compound LL; (iii) a specific activity against Compound GG greater than its specific activity against Compound DD; (iv) a specific activity against Compound Y greater than its specific activity against Compound B; (v) a specific activity against Compound A greater than its specific activity against Compound L; (vi) a specific activity against Compound X greater than its specific activity against Compound V; (vii) a specific activity against Compound JJ greater than its specific activity against Compound AA; (viii) a specific activity against Compound KK greater than its specific activity against Compound FF; (ix) a specific activity against Compound EE greater than its specific activity against Compound W; and (x) a specific activity against Compound HH greater than its specific activity against Compound I.

In a preferred aspect of the present invention, an extract is a purified extract. A purified extract may contain one or more enzymes or fragments thereof in purified form. A purified form includes any degree or type of purification. Any number of purification steps may be performed. In the context of the present invention, a purified extract may be partially purified, moderately purified, substantially purified, or fully purified. As used herein, a partially purified extract contains at least about 25% less activity on the cleavage of ANA (ANA activity) than the same extract that has not been subjected to any purification. A moderately purified extract contains at least about 50% less ANA activity than the same extract that has not been subjected to any purification. A substantially purified extract contains at least about 90% less ANA activity than the same extract that has not been subjected to any purification. A fully purified extract contains no detectable activity on the cleavage of ANA. In a preferred embodiment, a purified extract is fully purified. An extract that is partially, moderately, substantially, or fully purified may result from any number and combination of purification steps. An extract that is partially, moderately, or substantially purified may preferably be subjected to one or more further purification steps.

In a further preferred embodiment, a purified extract contains GS-9005 ester hydrolase A activity. In a preferred embodiment, a purified extract comprises GS-9005 ester hydrolase A or a fragment thereof. In another preferred embodiment, a purified extract comprises prolylcarboxypeptidase or a fragment thereof. In another preferred embodiment, a fully purified extract comprises prolylcarboxypeptidase-like activity. In another embodiment, a purified extract contains an enzyme that comprises or consists of one or more sequences selected from the group consisting of SEQ ID NO: 1, SEQ ID NO: 2, and fragments of either.

In another preferred embodiment, a purified extract contains only one enzyme with detectable ester hydrolase activity. In another preferred embodiment, a purified extract contains only one enzyme with detectable GS-9005 ester hydrolase A activity. In a preferred embodiment, a purified extract comprises only one enzyme with detectable GS-9005 ester hydrolase A activity, and the enzyme is GS-9005 ester hydrolase A. In a preferred embodiment, a purified extract comprises only one enzyme with detectable GS-9005 ester hydrolase A activity, and the enzyme is prolylcarboxypeptidase. In another embodiment, a purified extract comprises only one enzyme with detectable GS-9005 ester hydrolase A activity, and the enzyme is prolylcarboxypeptidase or a fragment or a homolog thereof. In an embodiment, an extract contains only one enzyme with detectable GS-9005 hydrolase A activity and the enzyme comprises or consists of a polypeptide sequence selected from the group consisting of SEQ ID NO 1, SEQ ID NO: 2, and fragments of either.

Fragments, Identity, and Homologs of Enzymes

One subset of the enzymes of the present invention is fragments of enzymes. In an embodiment, a fragment of an enzyme may be a polypeptide. As used herein, a polypeptide is any molecule that has three or more amino acid molecules joined by peptide bonds. A polypeptide may contain any additional chemical groups and may be folded into any conformation. In an embodiment, fragment molecules have ester hydrolase activity against a candidate compound. In a preferred embodiment, polypeptide molecules have ester hydrolase activity against a candidate compound and insignificant activity against alpha napthyl acetate. Fragments of an enzyme may consist of significant polypeptide sequences, or indeed most of the polypeptide sequences of, the enzymes of the present invention. Alternatively, the fragments may comprise smaller polypeptides, for example, having from about 3 to about 150 amino acids and more preferably, about 5 to about 15 amino acids, or about 20 to about 40 amino acids, or about 40 to about 70 amino acids, or about 70 to about 150 amino acids, or about 90 to about 120 amino acids.

In another aspect of the invention, one or more of the enzymes or fragments thereof of the invention share between about 100% and 70% sequence identity with one or more of the polypeptide sequences set forth in SEQ ID NO: 1 or SEQ ID NO: 2 or fragments of either. In a further aspect of the invention, one or more of the polypeptide molecules of the invention shares between about 100% and 90% sequence identity with one or more of the polypeptide sequences set forth in SEQ ID NO: 1 or SEQ ID NO: 2 or fragments of either. In an aspect of the invention, one or more of the polypeptide molecules of the invention shares between about 100% and 95% sequence identity with one or more of the polypeptide sequences set forth in SEQ ID NO: 1 or SEQ ID NO: 2 or fragments of either. In another aspect of the invention, one or more of the polypeptides of the invention shares between about 100% and 99% sequence identity with one or more of the polypeptide sequences set forth in SEQ ID NO: 1 or SEQ ID NO: 2 or fragments of either.

In a preferred embodiment, percent identity calculations are performed using the Megalign program of the LASERGENE bioinformatics computing suite (default parameters, DNASTAR Inc., Madison, Wis.).

Homologs are also included in the present invention. As used herein, a homolog or a fragment thereof is a counterpart molecule or fragment thereof in another species. A homolog can also be generated by molecular evolution or DNA shuffling techniques, so that the molecule retains at least one functional or structural characteristic of the original polypeptide (see, for example, U.S. Pat. No. 5,811,238).

The compounds of the present invention also include polypeptides that are fused to one another. The compounds of the present invention also include polypeptides that are introduced into host cells.

Conservative Substitutions

By the present invention, an enzyme or fragment thereof may include modifications made by one of ordinary skill in the art. For example, as will be apparent to the skilled art worker, a GS-9005 hydrolase A or fragment thereof may be modified such as by conservative amino acid changes within the polypeptide sequences of the invention. For example, it is contemplated that a GS-9005 hydrolase A or fragments thereof may be modified by conservative amino acid changes that do not diminish the ester hydrolase activity of the enzyme fragment thereof. Conservative changes that do not significantly diminish ester hydrolase activity may cause less than about a 25% reduction in ester hydrolase activity as compared to the enzyme with no conservative amino acid changes, less than about a 15% reduction in ester hydrolase activity as compared to the enzyme with no conservative amino acid changes, less than about a 15% reduction in ester hydrolase activity as compared to the enzyme with no conservative amino acid changes, less than about a 10% reduction in ester hydrolase activity as compared to the enzyme with no conservative amino acid changes, preferably less than about a 7% reduction in ester hydrolase activity as compared to the enzyme with no conservative amino acid changes, less than about a 5% reduction in ester hydrolase activity as compared to the enzyme with no conservative amino acid changes, less than about a 4% reduction in ester hydrolase activity as compared to the enzyme with no conservative amino acid changes, less than about a 3% reduction in ester hydrolase activity as compared to the enzyme with no conservative amino acid changes, less than about a 2% reduction in ester hydrolase activity as compared to the enzyme with no conservative amino acid changes, less than about a 1% reduction in ester hydrolase activity as compared to the enzyme with no conservative amino acid changes, or no detectable change in ester hydrolase activity as compared to the enzyme with no conservative amino acid changes.

In an embodiment, a GS-9005 hydrolase A or fragment thereof or an enzyme with GS-9005 hydrolase A activity comprises or consists of SEQ ID NO: 1, SEQ ID NO: 2 or fragments thereof and conservative substitution is made to SEQ ID NO: 1, SEQ ID NO: 2, or fragments thereof. Such changes permit optimization of codon usage, for example, if the GS-9005 hydrolase A or fragment or other enzyme of the invention or fragment thereof is introduced into a cell or organism. Conservative amino acid changes can be made by substituting one amino acid within one group with another amino acid in the same group. Conservative amino acid changes can also be made by substituting one or more codons with one or more different codons that produce the same amino acids. In this manner, conservative changes are made at the nucleotide level so that the same amino acid is coded for by a different nucleotide sequence. Biologically functional equivalents of the enzymes or fragments thereof of the present invention can have ten or fewer conservative amino acid changes, more preferably seven or fewer conservative amino acid changes, and most preferably five or fewer conservative amino acid changes. The encoding nucleotide sequence will thus have corresponding base substitutions, permitting the nucleotide sequence to encode biologically functional equivalent forms of the enzymes or fragments thereof of the present invention.

It is understood that certain amino acids may be substituted for other amino acids in a polypeptide without appreciable loss of interactive binding capacity with structures such as, for example, antigen-binding regions of antibodies or binding sites on substrate molecules. Certain amino acid sequence substitutions can be made in a polypeptide sequence and, of course, its underlying DNA coding sequence and, nevertheless, a polypeptide with like properties can be obtained. It is thus contemplated that various changes may be made in the polypeptide sequence of the enzymes or fragments thereof of the present invention, or corresponding DNA sequences that encode said polypeptides, without appreciable loss of their biological utility or activity. It is understood that codons capable of coding for such amino acid changes are known in the art.

In making changes to polypeptides of the present invention, the hydropathic index of amino acids may be considered. The importance of the hydropathic amino acid index in conferring interactive biological function on a protein is generally understood in the art (Kyte and Doolittle, *J. Mol. Biol.* 157, 105-132 (1982)). It is accepted that the relative hydropathic character of amino acids contributes to secondary structure, which in turn defines interaction with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J Mol. Biol.* 157, 105-132 (1982)); these are isoleucine (+4.5), valine (+4.2), leucine (+3.8), phenylalanine (+2.8), cysteine/cystine (+2.5), methionine (+1.9), alanine (+1.8), glycine (-0.4), threonine (-0.7), serine (-0.8), tryptophan (-0.9), tyrosine (-1.3), proline (-1.6), histidine (-3.2), glutamate (-3.5), glutamine (-3.5), aspartate (-3.5), asparagine (-3.5), lysine (-3.9), and arginine (-4.5).

In making such changes, the substitution of amino acids whose hydropathic indices are within ±0.2 is preferred, those within ±0.1 are particularly preferred, and those within ±0.5 are even more particularly preferred.

It is also understood in the art that the substitution of like amino acids can be made effectively on the basis of hydrophilicity. As detailed in U.S. Patent No.4,554,101, the following hydrophilicity values have been assigned to amino acid residues: arginine (+3.0), lysine (+3.0), aspartate (+3.0.±0.1), glutamate (+3.0.∓0.1), serine (+0.3), asparagine (+0.2), glutamine (+0.2), glycine (0), threonine (-0.4), proline (-0.5.±0.1), alanine (-0.5), histidine (-0.5), cysteine (-1.0), methionine (-1.3), valine (-1.5), leucine (-1.8), isoleucine (-1.8), tyrosine (-2.3), phenylalanine (-2.5), and tryptophan (-3.4).

In making such changes, the substitution of amino acids whose hydrophilicity values are within .+/−.0.2 is preferred, those which are within .+/−.0.1 are particularly preferred, and those within .+/−.0.0.5 are even more particularly preferred.

Nucleic Acid Molecules of the Present Invention

Nucleic acid molecules of the present invention include nucleic acid molecules or fragments thereof that encode an enzyme or fragment thereof of the present invention. In an embodiment, a nucleic acid molecule of the present invention encodes an enzyme or a fragment thereof with GS-9005 ester hydrolase A activity. In an embodiment, a nucleic acid molecule of the present invention encodes a GS-9005 ester hydrolase A enzyme or a fragment thereof.

In an embodiment, a nucleic acid molecule of the present invention encodes an enzyme that comprises or consists of SEQ ID NO: 1 or a fragment thereof. In another embodiment, a nucleic acid molecule of the present invention encodes an enzyme that comprises or consists of SEQ ID NO: 2 or a fragment thereof. In an embodiment, a nucleic acid molecule encodes an enzyme that does not comprise or consist of any sequence selected from the group consisting of SEQ ID NO: 1, SEQ ID NO: 2, and fragments of either.

In an embodiment, a nucleic acid molecule of the invention encodes prolylcarboxypeptidase or a fragment or a homolog thereof. In an embodiment, a nucleic acid molecule of the invention does not encode any member selected from the group consisting of prolylcarboxypeptidase, fragments thereof, and homologs thereof. In an embodiment, a nucleic acid molecule of the present invention encodes an enzyme or a fragment thereof with prolylcarboxypeptidase-like activity. In an embodiment, a nucleic acid molecule of the present invention does not encode any member selected from the group consisting of an enzyme with prolylcarboxypeptidase-like activity and a fragment thereof. In an embodiment, a nucleic acid molecule of the invention encodes prolylcarboxypeptidase or a fragment thereof. In another embodiment, a nucleic acid molecule of the invention encodes a homolog of prolylcarboxypeptidase or a fragment thereof. In an embodiment, a nucleic acid molecule of the invention does not encode any member selected from the group consisting of a homolog of prolylcarboxypeptidase and fragments thereof.

Fragments, Identity, and Homology of Nucleic Acid Molecules

One subset of the nucleic acid molecules of the invention is fragment nucleic acids molecules. Fragment nucleic acid molecules may consist of significant portions of, or indeed most of, the nucleic acid molecules of the invention. Alternatively, the fragments may comprise smaller oligonucleotides, for example oligonucleotides having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues.

With respect to nucleic acid molecules, as used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if the two molecules exhibit complete complementarity. As used herein, molecules are said to exhibit complete complementarity when every nucleotide of one of the molecules is complementary to a nucleotide of the other. Two molecules are said to be minimally complementary if they can hybridize to one another with sufficient stability to permit them to remain annealed to one another under at least conventional low-stringency conditions. Similarly, the molecules are said to be complementary if they can hybridize to one another with sufficient stability to permit them to remain annealed to one another under conventional high-stringency conditions.

Conventional stringency conditions are described by Sambrook et al., *Molecular Cloning, A Laboratory Manual*, 2$^{nd}$ Ed., Cold Spring Harbor Press, Cold Spring Harbor, N.Y. (1989) and by Haymes et al., *Nucleic Acid Hybridization, A Practical Approach, IRL Press*, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions, which promote DNA hybridization, for example, 6.0×sodium chloride/sodium citrate (SSC) at about 45° C., followed by a wash of 2.0×SSC at 20-25° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the invention will specifically hybridize to one or more of the nucleic acid molecules that encodes SEQ ID NO: 1 or SEQ ID NO: 2 or fragments of either under moderately stringent conditions, for example at about 2.0×SSC and about 65° C. In a particularly preferred embodiment, a nucleic acid of the invention will include those nucleic acid molecules that specifically hybridize to one or more of the nucleic acid molecules that encodes the polypeptide sequence set forth in SEQ ID NO: 1 or SEQ ID NO: 2 or fragments of either under high stringency conditions such as 0.2×SSC and about 65° C.

In another aspect of the invention, one or more of the nucleic acid molecules of the invention shares between about 100% and 70% sequence identity with one or more of the nucleic acid sequences that encode the polypeptide sequence set forth in SEQ ID NO: 1 or SEQ ID NO: 2 or fragments of either. In a further aspect of the invention, one or more of the nucleic acid molecules of the invention share between about 100% and 90% sequence identity with one or more of the nucleic acid sequences that encode the polypeptide sequence set forth in SEQ ID NO: 1 or SEQ ID NO: 2 or fragments of either. In an aspect of the invention, one or more of the nucleic, acid molecules of the invention share between about 100% and 95% sequence identity with one or more of the nucleic acid sequences that encode the polypeptide sequence set forth in SEQ ID NO: 1 or SEQ ID NO: 2 or fragments of either. In another aspect of the invention, one or more of the nucleic acid molecules of the invention share between about 100% and 99% sequence identity with a one or more of the nucleic acid sequences that encode the polypeptide sequence set forth in SEQ ID NO: 1 or SEQ ID NO: 2 or fragments of either.

A nucleic acid molecule of the invention can also encode a homologous polypeptide or a fragment thereof.

In another aspect of the present invention, one or more of the nucleic acid molecules of the present invention differ in nucleic acid sequence from those encoding a enzyme or fragment thereof due to the fact that one or more codons encoding an amino acid has been substituted for by a codon that produces the same amino acid originally encoded. Techniques of conservative substitution that may be employed may be those apparent to the artisan as well as those described, for example, herein supra.

The compounds of the present invention also include nucleic acid molecules that are fused to one another. The compounds of the present invention also include nucleic acid molecules that are introduced into host cells.

Purification of Extract Enzymes and Fragments Thereof

Following extraction, the enzymes or fragments thereof of the present invention can be separated or purified or both to the desired degree of homogeneity and activity by the techniques known in the art. An extract may be processed by any techniques that enhance one or more characteristics of the extract including for example, quantity, quality, purity, specific activity, or relative activity. Processing may enhance one or more characteristics of the extract while having any effect, including an advantageous effect, a detrimental effect, or no effect, on one or more other characteristics. In a preferred embodiment, an extract is a purified extract. A purified extract includes any extract that has been purified by any known method or combination of methods for purification.

A variety of techniques related to polypeptide purification will be apparent to the artisan. Numerous texts including Scope's *Protein purification: principles and practice* (Springer Verlag, New York (1997)), Harris' *Protein purification applications: a practical approach* (Oxford, N.Y. (1990)), and Deutscher's "Guide to protein purification" in *Methods in Enzymology* (Vol. 128, Academic Press, San Diego (1990)) provide guidance regarding protein purification. In addition, in a preferred embodiment, an extract may be purified by any one or more of the procedures in Examples 5-8 and variations thereof.

Separation and purification may involve, for example, multiphase extraction, crystallization from a solvent or solvent mixture, distillation, sublimation, or chromatography.

In one embodiment, chromatography techniques can be applied for purifying enzymes of the present invention. Chromatography can involve any number of methods including, for example: adsorption chromatography; affinity and immunoaffinity chromatography; size exclusion chromatography; ion exchange chromatography; partition chromatography; hydrophobic interaction chromatography (HIC); chromatofocusing; high, medium, and low pressure liquid chromatography; small scale analytical chromatography; simulated moving bed (SMB) and preparative thin or thick layer chromatography, as well as techniques of small scale thin layer chromatography; reverse-phase and normal phase chromatography; and gravity and flash chromatography.

In separating and purifying the enzymes of the present invention, techniques such as column purification, for example using ion exchange resin, may be used. Ion exchange resins contain charged groups. Resins may be acidic or basic in nature. Acid resins are cation exchangers, and basic resins are anion exchangers. Weak or strong cation and anion exchangers may be used. Non-limiting exemplary resins include CM cellulose/sephadex (a weak cation exchanger), SP sephadex (a strong cation exchanger), DE cellulose/sephadex (a weak anion exchanger), and QAE sephadex (a strong anion exchanger).

Techniques such as Q15 Anion Exchange, Concanavalin A (Con A) affinity, Chromatofocusing, HR Anion Exchange, Butyl Sepharose-HIC, Hydroxyapetite, Gel Filtration, Hydrophobic Interaction Chromatography (HIC), and Lentil Lectin are among those techniques contemplated. In an embodiment of the present invention, enzyme purification is achieved by the use of a Q15 Anion Exchange Column, followed by a Butyl Sepharose-HIC column. In an aspect of the present invention, an extract of the present invention is purified by consecutive applications of the enzyme mixture to one or more Q15 Anion Exchange Columns, Butyl Sepharose Columns, and Mono P columns, or a combination thereof. In a preferred embodiment, enzyme purification may be enhanced by Chromatofocusing Chromatography. In a highly preferred embodiment, enzyme purification is achieved by use of a Q15 column, followed by use of two separate Butyl Sepharose HIC columns, followed by a Mono P column.

Another class of separation and purification methods useful in the present invention involves treatment of a mixture with a reagent selected to bind to or render otherwise separable a desired product, unreacted starting material, reaction byproduct, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), and the like.

In applying the methods of the present invention, selection of appropriate methods of separation and purification depends on the nature of the materials involved, including for example, boiling point, and molecular weight in distillation and sublimation, presence or absence of polar functional groups or pH in chromatography, stability of materials in acidic and basic media in multiphase extraction, and the like. One skilled in the art will apply techniques most likely to achieve the desired separation or purification or both. Exemplary, non-limiting separation and purification methods are provided in the specification, examples, and figures, including at Examples 5-8.

An extract to be purified can be obtained from any source. In an embodiment, an extract to be purified may be generated by recombinant methods. In an alternative embodiment, the extract may be derived from a natural source, such as an organic source found in nature. Preferably, the extract is obtained from a mammalian source. In a highly preferred embodiment, the extract is obtained from peripheral blood mononuclear cells (PBMCs) having carboxylic ester hydrolase activity. An enzyme in an extract may be modified by any one or more chemical procedures. Modification by chemical procedure may include oxidation, reduction, hydrolysis, amidation, esterification phosphorylation, glycosylation, and the like or any other chemical manipulation that is within the comprehension of one of skill in the art.

In a preferred aspect, an extract of the present invention is purified from cellular extract of peripheral blood mononuclear cells (PBMCs) and shows ester hydrolase activity on a candidate compound but has insignificant ester hydrolase activity on the cleavage of alpha naphthyl acetate (ANA). In another preferred aspect, an extract of the present invention can be separated from non-specific esterases capable of cleaving ANA through any chromatography techniques known in the art, including but not limited to those methods exemplified in the specification, examples, and figures. See e.g., Examples 5-8. Preferably, a compound of the present invention can be separated from non-specific esterases capable of cleaving ANA through anion exchange chromatography, cation exchange chromatography, hydrophobic interaction chromatography (HIC), and lentil lectin chromatography.

In an aspect, purification may remove one or more unwanted components. In an embodiment, purification yields a purified extract that has less than about 95%, less than about 90%, less than about 80%, less than about 70%, less than about 60%, less than about 50%, less than about 40%, less than about 30%, less than about 20%, less than about 10%, less than about 5%, less than about 4%, less than about 3%, less than about 2%, or less than about 1% of the ester hydrolase activity of an unpurified extract against ANA. An unpurified extract is an extract that has not been subjected to any purification following extraction.

In a preferred aspect, purification produces a purified extract that has less than about 50% of the ester hydrolase activity of an unpurified cellular extract on the cleavage of ANA. More preferably, the purified extract of the present invention has less than about 40%, less than about 30%, less than about 20%, or less than about 10% of the ester hydrolase activity of the unpurified cellular extract on the cleavage of ANA. Even more preferably, the purified compound of the present invention has less than about 5% of the ester hydrolase activity of the unpurified cellular extract on the cleavage of ANA. Still more preferably, the purified compound of the present invention has less than about 4%, less than about 3%, less than about 2% or less than about 1% of the ester hydrolase activity of the unpurified cellular extract on the cleavage of ANA. In a highly preferred embodiment, a compound of the present invention shows no detectable ester hydrolase activity on ANA.

Ester hydrolase activity against any compound, including for example candidate compounds and alpha napthyl acetate, can be measured by any procedure or combination of procedures available to the artisan. In a preferred embodiment of the present invention, ester hydrolase activity is measured as described in Examples 2B and 3.

Purification may also enhance the proportion of a particular enzyme as compared with the proportion of that enzyme in the original extract. In an embodiment, concentration of a target enzyme in a purified extract may be compared with concentration of a target enzyme in an unpurified extract. Varying degrees of purification of a target enzyme may be achieved by the methods of the present invention. In an embodiment, after purification, the target enzyme may be about 2-fold to about 10,000-fold more pure than the target enzyme in the original enzyme composition as measured by the increase in concentration of the target enzyme. In another embodiment, after purification, the target enzyme may be about 50-fold to about 100-fold more pure than the target enzyme in the original enzyme composition as measured by the increase in concentration of the target enzyme. In another embodiment, after purification, the target enzyme may be about 101-fold to about 400-fold more pure than the target enzyme in the original enzyme composition as measured by the increase in concentration of the target enzyme. In another embodiment, after purification, the target enzyme may be about 401-fold to about 1500-fold more pure than the target enzyme in the original enzyme composition as measured by the increase in concentration of the target enzyme. In another embodiment, after purification, the target enzyme may be about 1700-fold to about 6200-fold more pure than the target enzyme in the original enzyme composition as measured by the increase in concentration of the target enzyme. In another embodiment, after purification, the target enzyme may be about 1501-fold to about 6500-fold more pure than the target enzyme in the original enzyme composition as measured by the increase in concentration of the target enzyme. In another embodiment, after purification, the target enzyme may be about 1000-fold to about 8500-fold more pure than the target enzyme in the original enzyme composition as measured by the increase in concentration of the target enzyme. In another embodiment, after purification, the target enzyme is more than about 10,000-fold pure than the target enzyme in the original enzyme composition as measured by the increase in concentration of the target enzyme.

In another embodiment, the specific activity of an enzyme may also be enhanced by purification. As such, purity of the target enzyme may be assessed by reference to specific activity of the target enzyme. The specific activity of an enzyme may be increased by any amount. In an embodiment, after purification, the target enzyme may be about 2-fold to about 10,000-fold more pure than the target enzyme in the original enzyme composition as measured by the increase in specific activity of the target enzyme. In another embodiment, after purification, the target enzyme may be about 50-fold to about 100-fold more pure than the target enzyme in the original enzyme composition as measured by the increase in specific activity of the target enzyme. In another embodiment, after purification, the target enzyme may be about 101-fold to about 400-fold more pure than the target enzyme in the original enzyme composition as measured by the increase in specific activity of the target enzyme. In another embodiment, after purification, the target enzyme may be about 401-fold to about 1500-fold more pure than the target enzyme in the original enzyme composition as measured by the increase in specific activity of the target enzyme. In another embodiment, after purification, the target enzyme may be about 1700-fold to about 6200-fold more pure than the target enzyme in the original enzyme composition as measured by the increase in specific activity of the target enzyme. In another embodiment, after purification, the target enzyme may be about 1501-fold to about 6500-fold more pure than the target enzyme in the original enzyme composition as measured by the increase in specific activity of the target enzyme. In another embodiment, after purification, the target enzyme may be about 1000-fold to about 8500-fold more pure than the target enzyme in the original enzyme composition as measured by the increase in specific activity of the target enzyme. In another embodiment, after purification, the target enzyme is more than about 10,000-fold pure than the target enzyme in the original enzyme composition as measured by the increase in specific activity of the target enzyme.

By the methods of the present invention, purification of an enzyme is preferably achieved while preserving concentration of one or more of the enzymes in an extract. The concentration of one or more enzymes may be preserved by any amount, where the preservation is measured relative to the concentration of the unpurified enzyme extract. In a preferred embodiment, the concentration of enzyme composition preserved is preferably at least about 0.2% of the concentration of enzyme in the unpurified enzyme extract, at least about 0.5% of the concentration of enzyme in the unpurified enzyme extract, at least about 1% of the concentration of enzyme in the unpurified enzyme extract, at least about 2% of the concentration of enzyme in the unpurified enzyme extract, at least about 5% of the concentration of enzyme in the unpurified enzyme extract, at least about 10% of the concentration of enzyme in the unpurified enzyme extract, at least about 15% of the concentration of enzyme in the unpurified enzyme extract, at least about 20% of the concentration of enzyme in the unpurified enzyme extract, at least about 25% of the concentration of enzyme in the unpurified enzyme extract, at least about 30% of the concentration of enzyme in the unpurified enzyme extract t, at least about 40% of the concentration of enzyme in the unpurified enzyme extract, at least about 50% of the concentration of enzyme in the unpurified enzyme extract, at least about 60% of the concentration of enzyme in the unpurified enzyme extract, at least about 70% of the concentration of enzyme in the unpurified enzyme extract, at least about 80% of the concentration of enzyme in the unpurified enzyme extract, at least about 90% of the concentration of enzyme in the unpurified enzyme extract, or even more preferably, more than about 90% of the concentration of enzyme in the unpurified enzyme extract.

Candidate Compounds

A candidate compound includes any organic compound that might be a substrate for an ester hydrolytic enzyme. Non-limiting exemplary candidate compounds include esters and amides such as for example, carboxyl esters (e.g., esterified carboxylates), thioesters (e.g. thiocarboxylic acid esters and thioesters of thiophosphonic acids), phosphate esters, sulfate esters, esterified phosphonates, and carboxyamides. Particularly preferred exemplary candidate compounds include those with an esterified carboxylate or an esterified phosphonate. In a preferred embodiment, a candidate compound will be hydrolyzed by an extract that has insignificant activity on alpha napthyl acetate. Candidate compounds may also include metabolites of candidate compounds. A metabolite is a compound that has been metabolized in vivo. Compounds that have been metabolized include compounds resulting for example from the oxidation, reduction, hydrolysis, amidation, esterification and the like of a candidate compound, primarily due to enzymatic processes. Metabolite structures can be determined in any fashion, including for example by conventional techniques such as MS, NMR, or IR analysis.

In a preferred embodiment, a candidate compound comprises an esterified carboxylate or an esterified phosphonate. In a preferred embodiment, a candidate compound comprising an esterified phosphonate group is monosubstituted with a hydroxyorganic acid linked to the phosphorus atom through an oxygen atom. In a preferred embodiment, the hydroxyorganic acid is in the alpha position.

In another preferred embodiment, a candidate compound is substituted with an amino acid group in which a carboxyl group of the amino acid is esterified. In a preferred embodiment, the amino acid group is in the alpha position. In a preferred embodiment of the present invention, a candidate compound is an amino acid phosphonoamidate, where a carboxyl group of the amino acid is esterified. In another preferred embodiment, a candidate compound is substantially stable against extracellular hydrolysis of the esterified group.

In a preferred embodiment, a candidate compound is a prototype compound. In a highly preferred embodiment, a candidate compound is formed by substituting a prototype compound with an esterified carboxyl or an esterified phosphonate group, where prior to substitution, the prototype compound is believed to have therapeutic activity against human immunodeficiency virus, cancer, or inflammation. Any of a variety of synthetic means apparent to the artisan may be used to substitute a prototype compound with an esterified carboxyl or an esterified phosphonate group.

Human immunodeficiency virus, within the context of the present invention, refers to that which is ordinarily understood in the art. In a preferred embodiment, human immunodeficiency virus is associated with white blood cells. Prototype compounds believed to have therapeutic activity against human immunodeficiency virus are described for example in the Physician's Desk Reference (See e.g., $58^{th}$ ed., Thomson PDR Pub., (2004) ISBN 1-56363-471-6).

Cancer, within the context of the present invention, refers to that which is ordinarily understood in the art. In a preferred embodiment, cancer is associated with white blood cells. In a more preferred embodiment, cancer is any type of leukemia. Prototype compounds believed to have therapeutic activity against cancer are described for example in the Physician's Desk Reference (See e.g., $58^{th}$ ed., Thomson PDR Pub., (2004) ISBN 1-56363-471-6).

Inflammation, within the context of the present disclosure refers to that which is ordinarily understood in the art. In a preferred embodiment, inflammation is inflammation associated with white blood cells. In a more preferred embodiment, inflammation is any form of tissue rejection such as solid organ transplant rejection, asthma, or any type of arthritis, such as preferably rheumatoid arthritis.

A prototype compound may be believed to have therapeutic activity on the basis of any information available to the artisan. For example, a prototype compound may be believed to have therapeutic activity on the basis of information contained in the Physician's Desk Reference. See supra. In addition, by way of non-limiting example, a compound may be believed to have therapeutic activity on the basis of experience of a clinician, structure of the compound, structural activity relationship data, $EC_{50}$, assay data, $IC_{50}$ assay data, animal or clinical studies, or any other basis, or combination of such bases. In another embodiment, a prototype compound is not a nucleoside and does not contain a nucleoside base.

A therapeutically-active compound is a compound that has therapeutic activity, such as for example, the ability of a compound to induce a specified response when administered to a subject or tested in vitro. Treatment of a disease or condition can include improvement of a disease or condition by any amount, including prevention, amelioration, and elimination of the disease or condition. Therapeutic activity may be conducted against any disease or condition, including in a preferred embodiment against human immunodeficiency virus, cancer, arthritis or any combination thereof. In order to determine therapeutic activity any method by which therapeutic activity of a compound may be evaluated can be used. For example, both in vivo and in vitro methods can be used, including for example, clinical evaluation, $EC_{50}$, and $IC_{50}$ assays, and dose response curves.

Candidate compounds for use with an assay of the present invention or identified by assays of the present invention as useful pharmacological agents can be pharmacological agents already known in the art or variations thereof or can be compounds previously unknown to have any pharmacological activity. Candidate compounds of the present invention can be naturally occurring or designed in the laboratory. Candidate compounds can comprise a single diastereomer, more than one diastereomer, a single enantiomer, or more than one enantiomer. The ester hydrolase compounds of the present invention can have more or less ester hydrolase activity on one or another diastereomer or one or another enantiomer of a candidate compound. In a preferred embodiment, a candidate compound comprises a diastereomer, upon which the ester hydrolase activity is higher than the ester hydrolase activity on any other diastereomers of that candidate compound. In another preferred embodiment, a candidate compound comprises an enantiomer, upon which the ester hydrolase activity is higher than the ester hydrolase activity on any other enantiomers of that candidate compound. In another preferred embodiment, a candidate compound comprises a single diastereomer. In another preferred embodiment, a candidate compound comprises a single enantiomer.

Candidate compounds can be isolated, as from microorganisms, animals or plants, for example, and can be produced recombinantly, or synthesized by chemical methods known in the art. If desired, candidate compounds of the present invention can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries. The other four approaches are applicable to polypeptide, non-peptide oligomer, or small molecule libraries of compounds and are preferred approaches in the present invention. See Lam, *Anticancer Drug Des.* 12: 145-167 (1997).

Methods for synthesis of molecular libraries are well known in the art (see, for example, DeWitt et al., *Proc. Nat. Acad. Sci. USA* 90: 6909-6913 (1993); Erb et al. *Proc. Natl. Acad. Sci. U.S.A.* 91: 11422 (1994); Zuckermann et al., *J. Med. Chem.* 37: 2678 (1994); Cho et al., *Science* 261: 1303 (1993); Carell et al., *Angew. Chem. Int. Ed. Engl.* 33: 2059 (1994); Carell et al., *Angew. Chem. Int. Ed. Engl.* 33: 2061 (1994); Gallop et al., *J. Med. Chem.* 37: 1233 (1994)). Libraries of compounds can be presented in solution (see, e.g., Houghten, *BioTechniques* 13: 412-421 (1992)), or on beads (Lam, *Nature* 354: 82-84 (1991)), chips (Fodor, *Nature* 364: 555-556 (1993)), bacteria or spores (Ladner et al., U.S. Pat. No. 5,223,409), plasmids (Cull et al., *Proc. Natl. Acad. Sci. USA* 89, 1865-1869 1992), or phage (Scott & Smith, *Science* 249: 386-390 (1990); Devlin, *Science* 249: 404-406 (1990)); Cwirla et al., *Proc. Natl. Acad. Sci. USA*, 97: 6378-6382 (1990); Felici, *J. Mol. Biol.* 222: 301-310 (1991); and Ladner et al., U.S. Pat. No. 5,223,409).

Methods of the Present Invention

In an embodiment, the present invention provides a method of identifying a candidate compound as a suitable prodrug. A suitable prodrug includes any prodrug that may be identified by the methods of the present invention. For example, in an embodiment, a suitable prodrug includes any prodrug that may be identified by the production of one or more metabolite compounds. In a preferred embodiment, a suitable prodrug is identified by the production of one or more metabolite compounds that have a phosphonic acid group or a carboxylic acid group instead of an esterified phosphonate group or an esterified carboxyl group present in the candidate compound. A suitable prodrug identified by a method of the present invention may be subjected to any desired use or analysis following identification. For example, a suitable prodrug may be analyzed for toxicity, suitability as a therapeutic agent, effective concentration, or any other characteristic. In an embodiment, a suitable prodrug identified by the present invention may be used to treat a sample or subject.

Any method apparent to the artisan may be used to identify a candidate compound. In an embodiment, identification of a prodrug is made by providing a candidate compound and recognizing the formation of one or more metabolites. Such assays may involve without limitation providing a candidate compound having an esterified phosphonate group or esterified carboxyl group, contacting the candidate compound with an extract capable of catalyzing the hydrolysis of a carboxylic ester to produce one or more metabolite compounds, and identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

In an embodiment, the methods of the present invention include providing a candidate compound. In an embodiment, the methods of the present invention further include contacting a candidate compound with an extract. In a preferred embodiment, the present invention contemplates contacting a candidate compound with an extract comprising GS-9005 ester hydrolase A or fragments thereof. In another preferred embodiment, the present invention contemplates contacting a candidate compound with an extract comprising prolyl-carboxypeptidase or a fragment or homolog thereof. However, a candidate compound may be contacted with any extract. A candidate compound may be contacted with an extract in any manner that permits the extract to interact with the candidate compound. As an example, a candidate compound may be contacted with an extract by mixing the candidate compound and the extract together in any container such as for example a tube or a vial. In an embodiment, a candidate compound is contacted with an extract in vitro. In another embodiment, a candidate compound is contacted with an extract in a cell-free environment. In a further embodiment, a candidate compound is contacted with an extract in cell culture, preferably in a peripheral blood mononuclear cell culture.

In a further embodiment, the methods of the present invention include identifying a candidate compound as a suitable prodrug if the extract has catalyzed the formation of one or more metabolite compounds. Analysis of metabolite compounds may be achieved by any method. For example, methods of analysis described in the specification or any other methods of analysis known to the skilled artisan may be used. Conventional techniques such as NMR, IR, including FT-IR, and titration may be used without limitation to identify a metabolite. The production of a metabolite compound may also be monitored by the use of a radioactive substrate to produce a radio-labeled metabolite as shown in Example 2A. In another aspect, ester hydrolase activity is preferably monitored by the production of a non-radio-labeled metabolite as in Example 2B. In the case of radioactive metabolites, methods including for example scintillation counting may be used to ascertain the specific activity of an ester hydrolase on a candidate compound. In the case on non-radio-labeled metabolites, ester hydrolase activity may be detected by techniques, including, for example, chromatography and mass spectrometry.

Cleavage of a prodrug by ester hydrolase activity can be compared with the $EC_{50}$ of the drug. In a preferred embodiment, a correlation is observed between ester hydrolase activity of a compound of the present invention and $EC_{50}$ of the drug. In a preferred embodiment, cleavage of a prodrug may be used as a predictor of drug activity or cell loading or both.

An enzyme or fragment thereof of the present invention that shows ester hydrolase activity against a candidate compound may be evaluated for activity against any other candidate compounds, including for example candidate compounds of the same drug class or of different drug classes.

The methods of the present invention may be conducted in vivo or in vitro. In a preferred aspect, the methods of the present invention are conducted using peripheral blood mononuclear cells (PBMCs). Peripheral blood mononuclear cells may be obtained from a patient who is or is not undergoing leukophoresis. In a preferred embodiment, the PBMCs are obtained from a patient who is undergoing leukophoresis.

In another aspect of the present invention, the activity of the ester hydrolase compounds of the present invention may be inhibited by any compound or agent that inhibits ester hydrolase activity. Exemplary inhibitors include fluorophosphonate, fluorophosphonate derivatives, isocoumarins such as 3,4 dichloroisocoumarin, and peptide carboxyl esters of chloro- and fluoro-methyl ketones. Inhibition of ester hydrolase activity may be ascertained by any techniques available to the artisan. In a preferred embodiment of the present invention, inhibition is measured by $IC_{50}$ assay as described in Example 12.

In another aspect, the present invention provides methods of screening candidate compounds for suitability as therapeutic agents. Screening for suitability of therapeutic agents may include assessment of one, some or many criteria relating to the compound that may affect the ability of the compound as a therapeutic agent. Factors such as, for example, efficacy, safety, efficiency, retention, localization, tissue selectivity, degradation, or intracellular persistence may be considered. In an embodiment, a method of screening candidate compounds for suitability as therapeutic agents is provided, where the method comprises providing a candidate compound identified as a suitable prodrug, determining the therapeutic activity of the candidate compound, and determining the intracellular persistence of the candidate compound. Intracellular persistence can be measured by any technique apparent to the skilled artisan, such as for example by radioactive tracer, heavy isotope labelling, or LCMS.

In a further preferred embodiment, a method of screening candidate compounds for suitability as therapeutic agents further comprises determining the tissue selectivity of the candidate compound or a metabolite, preferably an acid metabolite, of the candidate compound. Tissue selectivity refers to the propensity of one or more compounds, including for example a candidate compound or one or more metabolite compounds, to accumulate preferentially in one or more cells, tissues, or organs. Tissue selectivity may be evaluated by any of a variety of techniques apparent to the artisan. For example, tissue selectivity may be observed on the basis of a radioactive, fluorescent or other dye tag that has been added to a candidate compound. The accumulation of the tag in particular tissues may then be observed.

In an embodiment, the present invention provides a method of identifying a candidate compound as a suitable prodrug. A suitable prodrug includes any prodrug that may be identified by the methods of the present invention. For example, in an embodiment, a suitable prodrug includes any prodrug that may be identified by the production of one or more metabolite compounds. In a preferred embodiment, a suitable prodrug is identified by the production of one or more metabolite compounds that have a phosphonic acid group or a carboxylic acid group instead of an esterified phosphonate group or an esterified carboxyl group present in the candidate compound. A suitable prodrug identified by a method of the present invention may be subjected to any desired use or analysis following identification. For example, a suitable prodrug may be analyzed for toxicity, suitability as a therapeutic agent, effective concentration, or any other characteristic. In an embodiment, a suitable prodrug identified by the present invention may be used to treat a sample or subject.

In order to identify a candidate compound as a suitable prodrug, any method may be used. For example, in a preferred embodiment, a candidate compound may be identified as a suitable prodrug by providing a candidate compound having an esterified phosphonate group or esterified carboxyl group, contacting the candidate compound with an extract capable of catalyzing the hydrolysis of a carboxylic ester to produce one or more metabolite compounds, and identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

In an embodiment, a method of screening candidate compounds for therapeutic activity may also include determining the therapeutic activity of a candidate compound or any metabolites thereof or both. Therapeutic activity against any disease or condition may be assessed. In a preferred embodiment, therapeutic activity against human immunodeficiency virus (HIV) may be assessed. In another preferred embodiment, determining the therapeutic activity of a candidate compound comprises determining activity against HIV protease, HIV integrase, HIV reverse transcriptase, any other HIV enzyme, or any combination of such enzymes.

In another preferred embodiment, determining the therapeutic activity of a candidate compound comprises determining the resistance of HIV to the candidate compound or any metabolites thereof or both. In an embodiment, determining the therapeutic activity of a candidate compound may further include determining the anti-HIV activity of a metabolite of the candidate compound. In a preferred embodiment, a metabolite of the candidate compound is an acid metabolite, particularly preferably a carboxylic acid or phosphonic acid. Methods of determining the therapeutic activity of a candidate compound will be known to the artisan. Such methods may be performed in vitro or in vivo. Exemplary methods include those such as clinical evaluation, Ki, $EC_{50}$, $CC_{50}$, and $IC_{50}$ assays, as well as dose response curves and resistance studies. See e.g., Example 16.

In screening compounds for suitability as therapeutic agents, intracellular persistence of the candidate compound may also be evaluated. Evaluation of intracellular persistence may comprise, for example, evaluation of intracellular residence time or half-life of a compound. In a preferred embodiment, half-life of a compound in human tissue is determined. Half-life may be determined in any tissue. Preferred human tissues for determining half-life of a compound of the invention include without limitation helper cells, killer cells, lymph nodes, and peripheral blood mononuclear cells. Intracellular persistence, including for example, intracellular residence time of any metabolite compound, preferably an acid metabolite, may also be evaluated. Any technique known to the art worker for determining intracellular persistence may be used in the present invention. By way of non-limiting example, persistence of a compound may be measured by retention of a radiolabeled or dye labelled substance, including for example a candidate compound or a metabolite compound.

A further aspect of the present invention relates to methods of inhibiting the activity of a condition or disease comprising the step of treating a sample or subject believed to have a disease or condition with a prodrug identified by a compound of the invention. Compositions of the invention act as identifiers for prodrugs that have therapeutic activity against a disease or condition. In a preferred aspect, compositions of the invention act as identifiers for drugs that show therapeutic activity against conditions including for example cancer, inflammation, rheumatoid arthritis, and immunosuppression or any combination thereof. Compositions of the invention may also act as identifiers for drugs that have therapeutic activity against infectious agents. Infectious agents against which the therapeutic agents may be effective include, without limitation, bacteria, viruses, and yeast. In a non-limiting example, the enzymes may be useful to identify inhibitor prodrugs that bind to locations on the surface or in a cavity of HIV protease having a geometry unique to HIV protease.

If desired, after application of an identified prodrug, the amount of an infectious organism or the level or any material indicative of the infection or condition may be observed by any method including direct and indirect methods of detecting such level. Quantitative, semi-quantitative, and qualitative methods of determining such a level are all contemplated. Any method, including but not limited to, observation of the physiological properties of a living organism, are also applicable.

However, in some cases, for example when screening compounds capable of inhibiting HIV protease viruses, the results of enzyme assays may not correlate with cell culture assays. Thus, a cell-based assay should be the primary screening tool for use in the HIV context.

Cells

In an aspect of the present invention, a cell-based system can be used to screen for prodrug compounds. In one aspect, that cell-based system is a non-recombinant cell-based system. In an aspect of the present invention, the cells are fresh human peripheral blood mononuclear cells obtained from patients undergoing leukophoresis. In another aspect, the cells are fresh human peripheral blood mononuclear cells obtained from patients not undergoing leukophoresis. In a further aspect, a nucleic acid sequence or fragment thereof encoding a GS-9005 hydrolase A or fragment thereof, is used in a recombinant cell-based system. In another aspect, a nucleic acid sequence or fragment thereof encoding an enzyme with GS-9005 hydrolase A activity is used in a recombinant cell-based system.

Polynucleotides of the present invention encoding GS-9005 ester hydrolase A or a fragment thereof may be introduced into a host cell. A host cell strain may be chosen for its ability to modulate the expression of the inserted sequences or to process an expressed GS-9005 ester hydrolase A enzyme or fragment thereof in the desired fashion. Such modifications of GS-9005 ester hydrolase A or fragment thereof include, but are not limited to, acetylation, carboxylation, glycosylation, phosphorylation, lipidation, and acylation. Post-translational processing which cleaves a "prepro" form of the GS-9005 ester hydrolase A or fragment thereof also can be used to facilitate correct insertion, folding and/or function. A variety of host cells which have specific cellular machinery and characteristic mechanisms for post-translational activities (e.g., CHO, HeLa, MDCK, HEK293, and W138), are available from the American Type Culture Collection (ATCC 10801 University Boulevard, Manassas, Va. 20110-2209) and can be chosen to ensure the correct modification and processing of the foreign protein. Additional host cells may be maintained in the laboratory stock or be commercially available. Suitable host strains will be known to one of ordinary skill in the art.

In selecting a host cell, stable expression is generally preferred for long-term, high-yield production of recombinant polypeptides. For example, cell lines which stably express GS-9005 ester hydrolase A can be transformed using expression vectors which can contain viral origins of replication and/or endogenous expression elements and a selectable marker gene on the same or on a separate vector. Following the introduction of the vector, cells can be allowed to grow for 1-2 days in an enriched medium before they are switched to a selective medium. The purpose of the selectable marker is to confer resistance to selection, and its presence allows growth and recovery of cells that successfully express the introduced enzyme sequences. Resistant clones of stably transformed cells can be proliferated using tissue culture techniques appropriate to the cell type. See, for example, *Animal Cell Culture*, R. I. Freshney, ed., 1986.

Any number of selection systems can be used to recover transformed cell lines. These include, but are not limited to, the herpes simplex virus thymidine kinase (Wigler et al., *Cell* 11: 223-32 (1977)) and adenine phosphoribosyltransferase (Lowy et al., *Cell* 22: 817-23 (1980)) genes which can be employed in ti⁻ or aprt⁻ cells, respectively. Also, antimetabolite, antibiotic, or herbicide resistance can be used as the basis for selection. For example, dhfr confers resistance to methotrexate (Wigler et al., *Proc. Natl. Acad. Sci. USA*, 77: 3567-70 (1980)), npt confers resistance to the aminoglycosides, neomycin and G-418 (Colbere-Garapin et al., *J. Mol. Biol.*, 150: 1-14 (1981)), and als and pat confer resistance to chlorsulfuron and phosphinotricin acetyltransferase, respectively (Murray, 1992). Additional selectable genes have been described. For example, trpB allows cells to utilize indole in place of tryptophan, or hisD, which allows cells to utilize histinol in place of histidine (Hartman & Mulligan, *Proc. Natl. Acad. Sci USA*. 85: 8047-51 (1988)). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., *Methods Mol. Biol*. 55: 121-131 (1995)).

In addition to cell-based systems, a candidate compound can be screened in a non-transgenic or transgenic organism. In a preferred embodiment, the organism is a mouse, rat, dog, cat, rabbit, guinea pig, or monkey.

Mammalian Expression

Enzymes or fragments thereof or polynucleotides encoding enzymes or fragments thereof of the present invention may be expressed in mammalian systems. For example, a number of viral-based expression systems can be used to express enzymes or fragments thereof in mammalian host cells. If an adenovirus is used as an expression vector, sequences encoding enzymes or fragments thereof can be ligated into an adenovirus transcription/translation complex comprising the late promoter and tripartite leader sequence. Insertion in a non-essential E1 or E3 region of the viral genome can be used to obtain a viable virus which is capable of expressing an enzyme or fragment thereof in infected host cells (Logan & Shenk, *Proc. Natl. Acad. Sci. USA* 81: 3655-3659 (1984)). If desired, transcription enhancers, such as the Rous sarcoma virus (RSV) enhancer, can be used to increase expression in mammalian host cells.

Alternatively, in the present invention, human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used in the methods of the present invention to achieve more efficient translation of sequences encoding enzymes or fragments thereof Such signals include the ATG initiation codon and adjacent sequences. In cases where sequences encoding an enzyme or fragment thereof, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression of the enzymes or fragments thereof or polynucleotides or fragments thereof of the present invention can be enhanced by the inclusion of enhancers which are appropriate for the particular cell system which is used (See Scharf et al., *Results Probl. Cell Differ.* 20, 125-162, 1994).

Transgenic Animals

In an embodiment, a nucleic acid molecule encoding a GS-9005 ester hydrolase A enzyme or fragment thereof may be introduced into an animal in order to produce a transgenic animal. In another embodiment, a nucleic acid molecule encoding an enzyme or fragment thereof with GS-9005 ester hydrolase A activity may be introduced into an animal in order to produce a transgenic animal. Techniques to introduce such nucleic acids are known in the art. In a preferred embodiment, the transgenic animal is a mammal, including for example, a mouse, rat, dog, cat, rabbit, guinea pig, or monkey. Preferred specific tissues for expression in transgenic animals of the invention include liver, spleen, muscle, and blood. It may be preferable to specifically overexpress a GS-9005 ester hydrolase A enzyme or any polypeptide of the invention in specific blood cells, for example, PBMCs. Transgenic animals expressing or overexpressing a GS-9005 ester hydrolase A may be used for pharmacokinetic analysis and metabolite analysis. In another embodiment of the present invention, the transgenic animals express antisense constructs encoding a GS-9005 ester hydrolase A enzyme or any polypeptide of the invention. Such animals may be used to demonstrate the conversion of test compounds in one or more tissues.

The following examples are illustrative and not intended to be limiting in any way.

EXAMPLES

Example 1

Metabolism of Nucleotide Phosphoramidates

Figure 2:
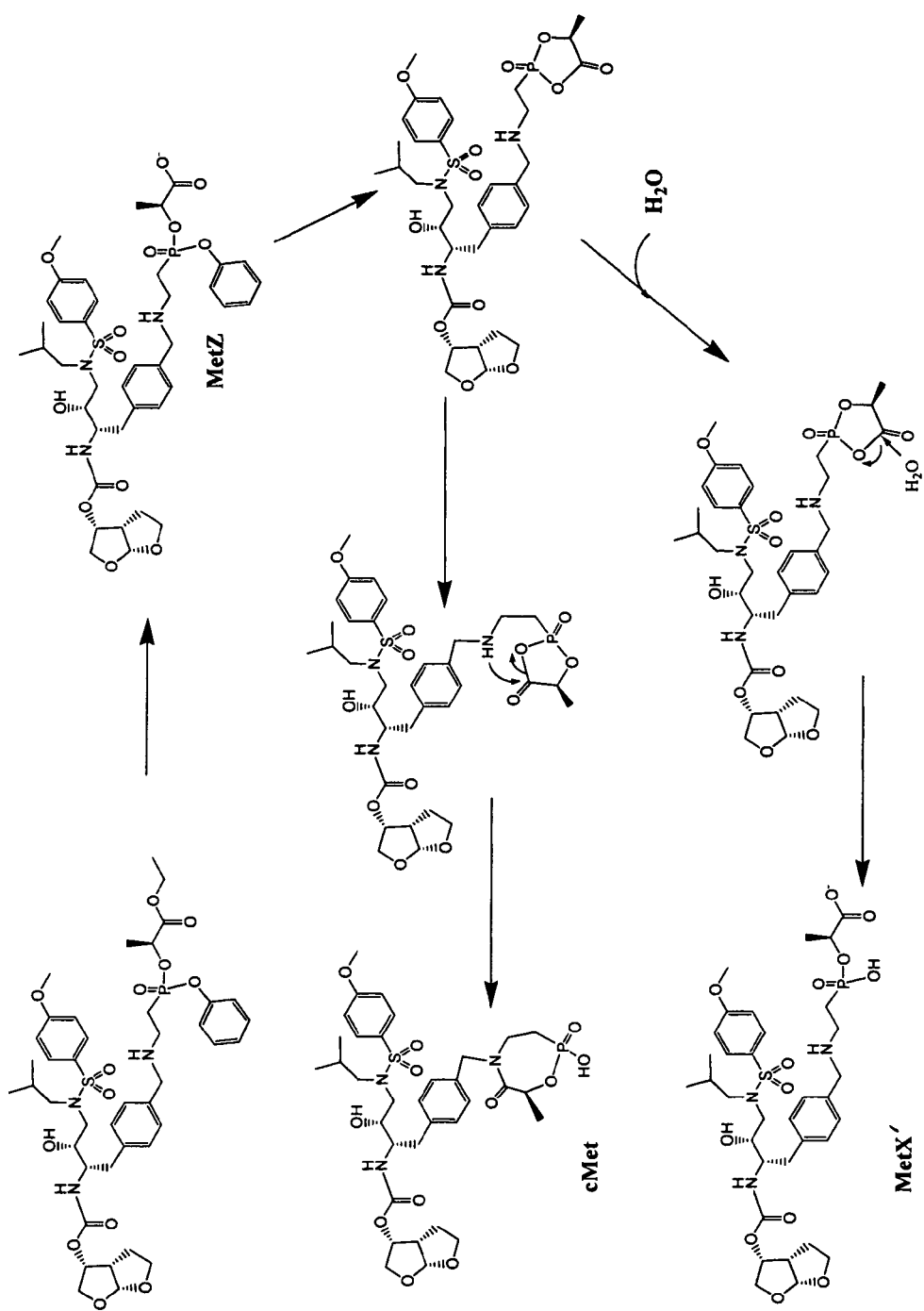
FIG. 2 depicts a scheme for the bioactivation of prodrugs.
Figure 3:
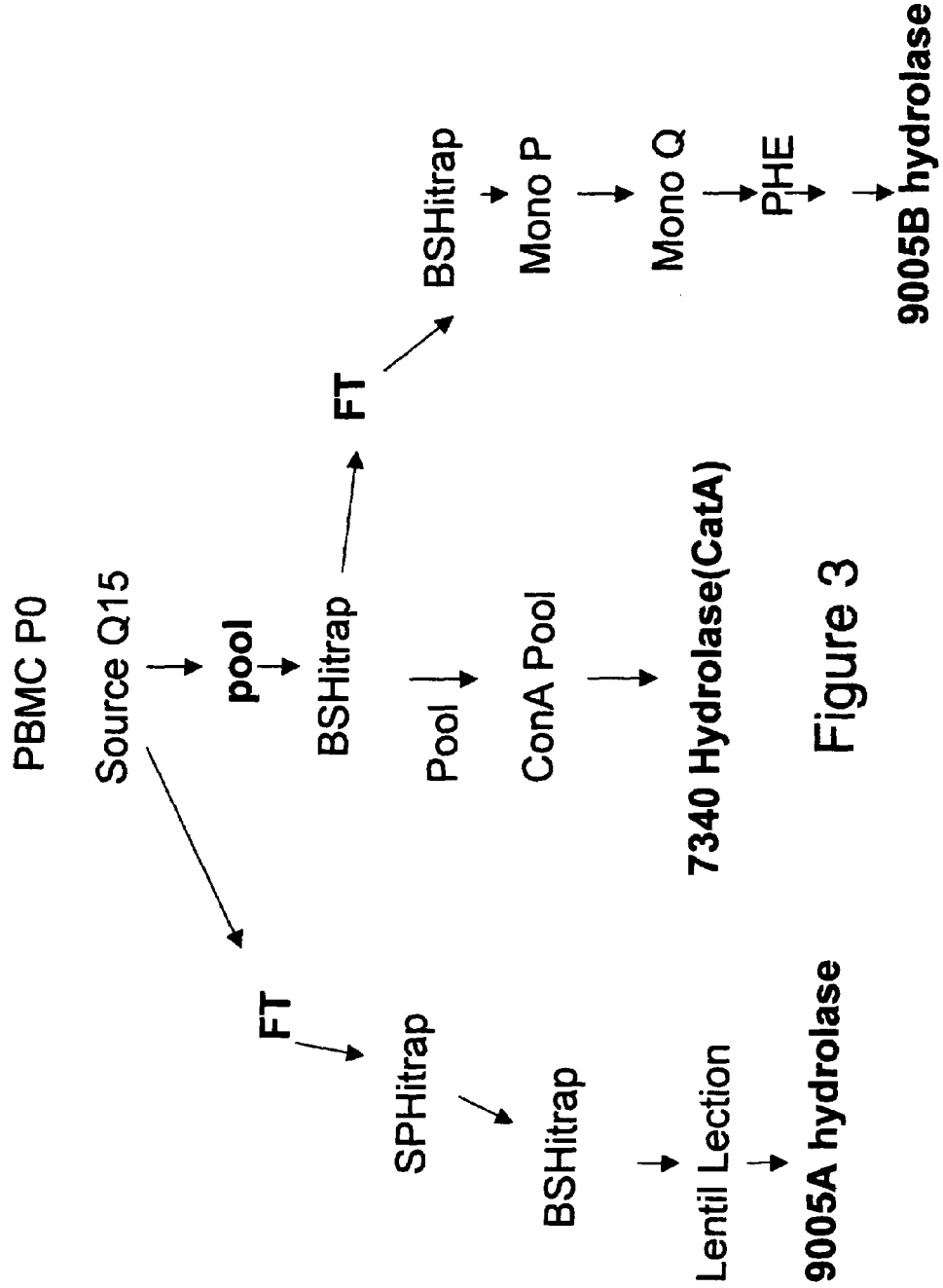
FIG. 3 depicts an exemplary hydrolase purification.

The efficient conversion of Compound L (Table 1) to its intracellular depot forms, cMetabolite (cMet) and Metabolite X' (MetX'), occurs via hydrolysis of the ethoxyl ester of Compound L (FIG. 2). A nucleophilic attack by the oxygen of the phenyl ester results in the formation of a 5-membered cyclic intermediate A. Intermediate A undergoes tranformation by two alternative pathways to intercellular depot forms, cMetabolite and Metabolite X'. In one pathway, the intermediate A is believed to undergo an intramolecular rearrangement involving the 5-membered ring to form cMet. In another pathway, the 5-membered ring of intermediate A is opened by the addition of water to form MetX'. cMetabolite and Metabolite X' may accumulate in cells, such as peripheral blood mononuclear cells (PBMCs) for example. Cellular accumulation of cMet and MetX' can be measured as in Examples 2A and 2B. In the case of other drug scaffolds with phosphonate prodrug moieties, cleavage of the carboxylic ester present in the phosphonate can also be expected to be a necessary step for the accumulation of the corresponding cMetabolite and Metabolite X' products. Purification of GS-9005 ester hydrolase A, which cleaves Compound L and other phosphonate prodrug substrates containing an amino acid-like carboxyl or phosphonate ester to form cMetabolite and Metabolite X', is described in the examples that follow.

Example 2

Ester Hydrolase Assay

A. Rate of Production of [$^{14}$C] cMetabolite Plus [$^{14}$C] Metabolite X':

The enzymatic production of cMetabolite (cMet) and Metabolite X' (Met X') from the Compound L is monitored using the following ester hydrolase assay. Varying amounts of peripheral blood mononuclear cell (PBMC) extracts, column fractions or pools are incubated with [$^{14}$C] Compound L at 37° C. for 10-90 min. The production of [$^{14}$C] cMetabolite and [$^{14}$C] Metabolite X' is monitored by measuring the amount of radioactivity retained on an anion exchange resin (DE-81). High performance liquid chromatography (HPLC) and mass spectrometry (MS) analysis of the reaction mixture and radioactivity retained on the filter confirm that only [$^{14}$C]-cMetabolite and [$^{14}$C]-Metabolite X' bind the DE-81 filter. Under the assay conditions, the more hydrophobic [$^{14}$C] Compound L is not retained on the DE-81 membrane. The final reaction conditions are 25 mM 2-[N-morpholino]ethanesulfonic acid (MES), pH 6.5, 100 mM NaCl, 1 mM DTT, 30 µM [$^{14}$C] Compound L substrate, 0.1% NP40 and varying amounts of GS-9005 ester hydrolase A enzyme in a final volume of 60 µl. The reaction mixture is incubated at 37° C. and at 10, 30 and 90 minutes, and 17 µl of the reaction mixture is spotted onto a DE-81 filter. The filter is washed with 25 mM Tris, pH 7.5 100 mM NaCl, dried at room temperature, and placed in vials containing 5 ml of scintillation fluid. [$^{14}$C]-cMetabolite and [$^{14}$C]-Metabolite X' present on the filters is determined using a scintillation counter (LS 6500, Beckman, Fullerton, Calif.). Activity is expressed as pmoles of the sum of cMetabolite plus Metabolite X' produced per minute per volume enzyme sample. GS-9005 ester hydrolase A specific activity is expressed as pmoles of the sum of cMetabolite plus Metabolite X' produced/minute/µg protein.

B. Rate of Production of cMetabolite Plus Metabolite X':

The enzymatic production of cMetabolite and Metabolite X' from non-radioactive Compound L and other prodrug compounds is also monitored using the following HPLC assay. Varying amounts of peripheral blood mononuclear cell (PBMC) extracts, column fractions or pools are incubated with non-radioactive compound substrates at 37° C. for 10-90 min. cMetabolite and Metabolite X' are extracted from the reaction mixture and separated from the parent prodrug using HPLC. Reaction mixtures contain 25 mM MES (pH 6.5), 100 mM NaCl, 1 mM DTT, 0.1% NP-40, 30 µM substrate, varying amounts of enzyme in a final volume of 100 µl. The enzymatic reaction is performed at 37° C. for 10-90 minutes and stopped by adding 180 µl of ice cold methanol. Samples are incubated at −20° C. for 30 min, and centrifuged 13,000 RPM for 30 min at 4° C. The supernatant is transferred to a 96-well plate and evaporated under vacuum using a speedvac. The precipitate is dissolved in 100 µl of buffer A (25 mM potassium phosphate, pH 6.0, 5 mM TBAB). Bound substrate and the Metabolite X' and cMetabolite products are monitored at 260 nm, and resolved using a 20 column volume (CV) gradient of buffer B (25 mM potassium phosphate, pH 6.0, 5 mM TBAB, 60% acetonitrile ($CH_3CN$). Metabolite X' product and cMetabolite product (identified by the retention time of synthesized Metabolite X', cMetabolite and mass spectrometry) consistently elute earlier than the prodrug substrate and are quantitated by integration of peak area. Activity is expressed as pmoles of the sum of cMetabolite plus Metabolite X' produced/minute/volume enzyme sample. GS-9005 ester hydrolase A specific activity is expressed as pmoles of the sum of cMetabolite plus Metabolite X' produced/minute/µg protein.

Example 3

Non-Specific Esterase Assay

Non-specific ester hydrolase activity is monitored by monitoring the enzymatic cleavage of alpha napthyl acetate (ANA) (Mastropaolo and Yourno, *Anal. Biochem.* 115:188-193 (1981)). This substrate has been used for both the measurement of esterase enzyme activity and in situ staining of esterases in tissue samples (Yourno and Mastropaolo, *Blood* 58:939-946 (1981); Yourno et al., *Blood* 60:24-29 (1982); Yourno et al., *J. Histochem. Cytochem.* 34:727-733 (1986)). The method described is a modification of the assay described by Mattes and Mattes, *Toxicol. Appl. Pharmacol.* 114: 71-76 (1992). Varying amounts of peripheral blood mononuclear cell (PBMC) extracts, column fractions, or pools are incubated with ANA at 37° C. for 20 min. The final reaction conditions are: 10 mM sodium phosphate, pH 6.5, 97 µM ANA and varying amounts of GS-9005 ester hydrolase A in a final volume of 150 µl. The reaction mixture is incubated at 37° C. for 20 minutes, and the reaction is stopped by the addition of 20 µl of 10 mM Blue salt RR in 10% sodium dodecyl sulfate (SDS). The alpha napthyl-Blue salt RR product is detected by reading absorbance at 405 nm. Activity is expressed as pmoles product produced per minute per volume enzyme sample.

Example 4

Isolation of GS-9005 Ester Hydrolase A

Extraction from Human PBMCs:

Fresh human PBMCs are obtained from patients undergoing leukophoresis; cells are shipped in plasma and processed within 26 h of draw. PBMCs are harvested by centrifugation at 1200×g for 5 minutes and washed three times by re-suspension in RBC lysis buffer (155 mM $NH_4Cl$, 1 mM EDTA, 10 mM $KHCO_3$). Washed cells ($29 \times 10^9$) are suspended in 150 ml of lysis buffer (10 mM Tris, pH 7.4, 150 mM NaCl, 20 mM $CaCl_2$, 1 mM DTT and 1% NP40) and incubated on ice for 20 minutes. The PBMC crude extract is centrifuged at 1000×g for 30 min to remove unlysed cells and the supernatant is centrifuged at 100,000×g for 1 hour. The 100,000×g supernatant (PBMC Extract: P0) is harvested (165 ml) and the pellets (1000×g and 100,000×g pellets) are resuspended in 10 mM Tris, pH 7.4, 150 mM NaCl, 20 mM $CaCl_2$, 1 mM DTT and assayed for GS-9005 ester hydrolase A activity. The crude PBMC extract, P0 PBMC extract (from 100,000×g supernatant) and the unsolubilized pellet (100,000×g pellet) are assayed as previously described using Compound L as the substrate. cMetabolite and Metabolite X' are quantitated using the HPLC assay described above. Assays show that less than 2% of the GS-9005 total ester hydrolase enzymatic activity is present in the pellets. The cell extract is snap frozen in liquid nitrogen and stored at −70° C.

Example 5

Anion Exchange Chromatography

The PBMC Extract ($15 \times 10^9$ cells, 75-85 ml) is diluted (1:10, vol: vol) with 25 mM Tris, pH 7.5, 10% glycerol, 1 mM DTT (Q15 Buffer A) and loaded onto an anion exchange column (2.5 cm×8.0 cm, Source Q15 (Amersham Biosciences, Piscataway, N.J.)), previously equilibrated with Q15Buffer A. Bound protein is eluted with a linear NaCl gradient (30 column volumes (CV)) to 0.5 M NaCl. Eluting protein is detected by monitoring absorbance at 280 nm. Fractions (12.0 ml) are collected and assayed for both GS-9005 ester hydrolase and ANA esterase activity. GS-9005 ester hydrolase activity elutes as a single major peak at 50-75 mM NaCl. Recovery of GS-9005 activity in the eluted fractions is 50% of total activity loaded and is attributed to GS-9005 ester hydrolase B, described in co-pending PCT Application entitled "Methods and Compositions for Identifying Therapeutic Compounds", filed Oct. 22, 2004, as attorney docket number 18477.040. The remaining 50% of the total GS-9005 ester hydrolase activity is attributable to GS-9005 ester hydrolase A and is recovered in the flow through of the Q15 column (Q15 FT). Significant ANA esterase activity (30-40% of total activity loaded) is detected in the column flow through; however, approximately 30% elutes in two peaks at 70-100 mM NaCl. The Q15 flow through containing GS-9005 hydrolase A activity and fractions containing GS-9005 hydrolase B activity (Q15 pool) are each individually snap frozen in liquid nitrogen and stored at −70° C.

Example 6

Cation Exchange Chromatography

The Q15 flow through containing GS-9005 hydrolase A (3000 ml from $30 \times 10^9$ PBMC cells) is adjusted to 25 mM MES, pH5.5 by adding 1/40 volume of 1 M MES pH 5.5, and the pH is adjusted with HCl prior to loading onto an SP-Sepharose column. DTT is added to a final concentration of 1 mM. The sample is loaded onto an SP-Sepharose column (3×5 ml SP HP HiTrap, Amersham, Piscataway, N.J.) previously equilibrated with 25 mM MES pH 5.5, 10% glycerol, 1 mM DTT (SP Buffer A). The column is washed with approximately 500 ml of SP Buffer A and bound protein is eluted with a linear gradient of 25 CV to 100% 25 mM MES pH 5.5, 0.5 M NaCl, 10% glycerol, 1 mM DTT (SP Buffer B). Fractions (12.5 ml) are collected and assayed for both GS-9005ester hydrolase A and ANA esterase activity. GS-9005 ester hydrolase A activity elutes as a single major peak at 100-125 mM NaCl. Recovery of total GS-9005 ester hydrolase A activity in the eluted fractions is 50-60% of total activity loaded. No GS-9005 hydrolase A activity is recovered in the flow through of the SP column. Significant ANA Esterase activity (60-65% of total activity loaded) is detected in the column flow through; however, approximately 30% eluted in a single peak at 70-100 mM NaCl. The GS-9005 hydrolase SP pool is snap frozen in liquid nitrogen.

Example 7

Hydrophobic Interaction (HIC) Chromatography

The SP pool is defrosted and diluted 1:1 (vol:vol) with 3M ammonium sulfate $(NH4)_2SO_4$. 1.0M Tris, pH 8.0, and 1.9M DTT are added to final concentrations of 100 mM and 1 mM, respectively. The sample (300 ml/$10 \times 10^9$ cells) is loaded onto a Butyl Sepharose HIC column (2×5 ml HiTrap, Amersham Biosciences, Piscataway, N.J.) previously equilibrated with 25 mM Tris, pH 8.0, 1.5M $(NH_4)_2SO_4$, 1 mM DTT, 10% glycerol (BS-HIC Buffer A2). Bound protein is eluted with a linear gradient (25 CV) with 25 mM Tris, pH 8.0, 1 mM DTT, 10% glycerol. Eluting protein is detected by monitoring absorbance at 280 nm. Fractions (4.0 ml) are collected and assayed for both GS-9005 ester hydrolase A and ANA esterase activity. GS-9005 hydrolase A activity elutes as a single major peak at 0.75 M (NH4)2SO4. Recovery of total GS-9005 hydrolase A activity in the eluted fractions is 50-65% of total activity loaded. Significant ANA esterase activity (85-90% of total activity loaded) is detected in the column flow through; however, approximately 10-15% eluted in a peak at 0.5M (NH4)2SO4. Fractions containing GS-9005 ester hydrolase A activity (BS-HIC pool) are pooled, snap frozen in liquid nitrogen and stored at −70° C.

Example 8

Lentil Lectin Affinity Chromatography

The BS-HIC pool (80-100 ml/10×10$^9$ cells) is defrosted, and diluted (1:1, vol:vol) 20 mM Tris, pH 7.5, 0.5M NaCl, 5 mM MnCl$_2$, 5 mM CaCl$_2$ (Lentil Lectin (LL) Buffer A). The sample containing the GS-9005 hydrolase A activity is loaded on a Lentil Lectin column (1.0 ml) previously equilibrated with Con A Buffer A. Bound protein is eluted sequentially with LL Buffer B (LL Buffer A +1M methyl-α1-manno-pyrraniside) and 100 mM Boric Acid, pH 6.5. Eluting protein is detected by monitoring absorbance at 280 nm. Fractions (0.5 ml) are collected and assayed for GS-9005 hydrolase A activity. Recovery of total GS-9005 hydrolase A activity in the eluted fractions is 20-30% of total activity loaded. Fractions containing GS-9005 hydrolase A (LL pool) are snap frozen in liquid nitrogen and stored at −70° C.

Example 9

Summary of GS-9005 Ester Hydrolase Purification

The following table summarizes the purification of GS-9005 hydrolase A achieved. Protein is measured by a Coomassie Blue stain colorometric assay (Bradford Protein Assay, BioRad, Hercules, Calif.). A 3800-6000 fold purification is achieved from the PBMC extracts. Overall recovery of GS-9005 hydrolase A from PBMC extracts is approximately 5-6%.

TABLE 2

Purification Summary of GS-9005 Ester Hydrolase A

| Sample | volume (ml) | Protein (mg/ml) | Total Protein (mg) | % Recovery |
|---|---|---|---|---|
| P0 | 4000 | 1.0 | 4000 | |
| Q FT (SP Load) | 4900 | 0.2 | 980 | 50 |
| SP Pool (BS Load) | 250 | 0.5 | 125 | >100 |
| BS Pool | 200 | 0.35 | 30 | 69 |
| Lentil Lectin Load A | 110 | 0.35 | 16.5 | 45 |
| Lentil Lectin Pool | 40 | | 0.05 | 25 |
| Estimated 9005 Hydrolase A in LL pool | 40 | | 0.01 | 5-6 |

Example 10

SDS-PAGE Resolution and Identification of Proteins in Lentil Lectin Pool

The Lentil Lectin pool containing purified GS-9005 hydrolase A is concentrated to approximately 60 μl (10 kDa MWCO Viva cell, Viva Science, Carlsbad, Calif.). Aliquots (10 μl and 50 μl) are loaded in adjacent lanes onto an SDS-PAGE gel (4-20% acrylamide gradient, NUPAGE; Invitrogen, Inc, Carlsbad, Calif.) and proteins are resolved according to the manufacturer's instructions. Protein bands in the 10 μl lane are visualized using silver staining and the adjacent areas of the gel in the unstained lane (50 μl aliquot) corresponding to a stained protein band are excised. In-gel digestion of proteins is performed in 50 mM ammonium bicarbonate containing excess trypsin at 37° C. overnight.

The resultant peptides are purified by passage through a C$_{18}$ ZipTip and analyzed by positive ESI-mass spectrometry (ESI-MS) using a Sciex Q-Star/Pulsar mass spectrometer (ABI Biotechnologies, Foster City, Calif.). Samples are introduced using a nanospray needle and data is collected in the MCA mode. Peptides are sequenced using MS/MS fragmentation. Proteins are identified from the generated sequences by blast analysis of the NCBI nr protein/peptide database. All of the visualized proteins are identified using this technique. A prominent protein band migrating with an apparent MW of 55-60 kDa yields peptides with the sequence N A I/L D P M S V . . . and N A I/L D P. This band represents approximately 20% of the total protein present in the Lentil Lectin Pool. The peptide sequences match the sequence of human prolylcarboxypeptidase (Accession #GI: 4826940). The identity of GS-9005 hydrolase A as human prolylcarboxypeptidase is supported by comparing the biochemical characteristics of the native enzymatic activity with those reported for the native enzyme. Recombinant prolylcarboxypeptidase is expressed and the relative rates of cleavage of the carboxylic ester bond present in different phosphonate produgs (structure activity relationship, SAR) are compared. Both native and recombinant enzymes are used in such expressions.

Example 11

Determination of Molecular Weight of GS-9005 Hydrolase in Aqueous Buffer

High Resolution Gel Filtration Chromatography:

An aliquot (5.0 ml) of the Q15 FT is defrosted, concentrated to 0.05 ml using a 5 kDa molecular weight cutoff concentrator (20 ml Vivaspin concentrator, Viva Science, Carlsbad, Calif.), and loaded onto a high resolution Gel Filtration column (8 mm×300 mm, KW 802.5; Shodex, Thomas Instrument Co., Oceanside, Calif.), previously equilibrated with 25 mM Tris, pH 7.5, 150 mM NaCl, 10% glycerol, 20 mM CaCl$_2$, 1 mM DTT (KW 802.5 column buffer). Eluting protein is detected by monitoring absorbance at 280 nm. Fractions (0.5 ml) are collected and assayed for GS-9005 hydrolase A. GS-9005 hydrolase A activity elutes as a single major peak in fractions corresponding to an apparent molecular weight of approximately 100 kDa. Recovery of total GS-9005 hydrolase A activity in the eluted fractions is approximately 40% of total activity loaded.

TABLE 3

Biochemical Characterization of GS-9005 Hydrolase A v Human Prolylcarboxypeptidase

| | 9005 Hydrolase A | IC$_{50}$ (μM) | ProlylcarboxyPeptidase |
|---|---|---|---|
| Native MW | ~100 kDa | | 115 kDa |
| Isoelectric point (pI) | 7.0-7.4 | | 7.0 |
| Cleavage of Cbz-pro-ala | ++ | | ++ |
| Inhibition profile | PMSF | 200 | 100-300 |
| | DFP | 10 | ++ |
| | Cbz-pro-pro-COH | 1.0 | 1.0 |

Example 12

Inhibition of GS-9005 Ester Hydrolases by Serine Hydrolase Inhibitors

Fluorophosphonate derivatives (Diisopropylfluorophosphate (DFP)) derivatives, isocoumarins such as 3,4 dichloroisocoumarin (3,4-DCI) and peptide carboxyl esters of chloro- and fluoro-methyl ketones (AlaAlaProAla-CMK, AlaAlaProVal-CMK, PheAla-FMK) are known effective inhibitors of serine hydrolases (Powers, J C and Harper, J W, *Inhibitors of Serine Proteinases* in *Proteinase Inhibitors*, 55-152, (Barrett and Salvesen, eds., Elsevier, Amsterdam, New York, Oxford, (1986)); Delbaere and Brayer, *J. Mol. Biol.* 183: 89-103 (1985); Bullock et al., *J. Mol. Biol.* 255: 714-725 (1996); Yongsheng et al., *Proc. Natl. Acad. Sci. USA* 96: 14694-14699 (1999); Kam et al., *Bioconjugate Chem.* 4: 560-567 (1993)). Carboxybenzoyl-Pro-Pro-COH (Cbz-PP-COH) is a specific inhibitor of prolylcarboxypeptidase. (H. Yokosawa, M. Nishikata and S. Ishii, "N-Benzyloxycarbonyl-Valyl-Prolinal, A Potent Inhibitor Of Post-Proline Cleaving Enzyme" *Journal of Biochemistry*, 95(6) 1819-1821 (1984)).

Inhibition of the enzymatic production of cMetabolite and Metabolite X' from Compound L is monitored using the following ester hydrolase inhibition assay. Varying amounts of purified GS-9005 hydrolase A and control enzymes (human leukocyte elastase (huLE) and porcine liver carboxylesterase (PLCE)) are incubated with Compound L in the presence and absence of varying amounts of known serine hydrolase inhibitors and Cbz-PP-COH at 37° C. for 10-90 min. The final reaction buffer conditions are 25 mM 2-[N-morpholino]ethanesulfonic acid (MES), pH 6.5, 100 mM NaCl, 1 mM DTT, and 0.1% NP40.

The production of cMetabolite and Metabolite X' is monitored using the HPLC assay described above in Example 2B. Activity is expressed as pmoles of the sum of cMetabolite plus Metabolite X' produced/minute/volume enzyme sample. Inhibition of ester hydrolase is expressed as percent activity present at a given concentration of inhibitor compared to hydrolase activity in the absence of the inhibitor. The results of the inhibition experiments are shown in Table 3 above.

Example 13

Active Site Labeling, Tryptic Digestion and Identification of 9005 Hydrolase A

Figure 4:
FIG. 4 depicts identification of serine hydrolase in a 9005 hydrolase A fraction labeled with AX4870 probe.

Biochemical characterization of GS-9005 hydrolase A indicates that the enzyme is inhibited by both Cbz-pro-pro-COH and DCI, known serine hydrolase inhibitors. AX4870 (ActivX, La Jolla, Calif.) is a serine hydrolase inhibitor with a fluorescent label that forms a covalent bond with the serine in the active site. Fractions containing 9005 hydrolase A (BS HIC fraction) are incubated with 30 µM AX4870 for 10 min at room temperature. Aliquots of the reaction mixture are analyzed by SDS-PAGE and labeled serine hydrolases are visualized using a fluoro-imager. A major serine hydrolase band is visualized (FIG. 4).

The bulk of the reaction mixture is incubated in 50 mM ammonium bicarbonate containing excess trypsin at 37° C. overnight. The resultant active site peptides are captured by passage through an antibody affinity column using antibodies specific for the AX4870 probe. The peptides are analyzed by positive ESI-mass spectrometry (ESI-MS) using a Sciex Q-Star/Pulsar mass spectrometer (ABI Biotechnologies, Foster City, Calif.). Samples are introduced using a nano-spray needle and data is collected in the MCA mode. Peptides are sequenced using MS/MS fragmentation. A serine hydrolase is identified by comparing the generated active site sequence with the known sequences of serine hydrolases in the NCBI nr protein/peptide database (FIG. 4 and Table 4).

A prominent band migrating with a MW of about 55kDa is identified as lysosomal prolylcarboxypeptidase proform (SEQ ID NO: 1) and mature form (SEQ ID NO: 2). It has been demonstrated that prolylcarboxypeptidase (PCP) exists as a homodimer in cells. Since biochemical characterization of 9005 hydrolase A indicates that its molecular weight on gel filtration is about 100 kDa, it is likely that 9005 hydrolase A is human PCP. PCP is identified in the Lentil Lectin pool (see above), and the published biochemical properties of PCP match those of 9005 hydrolase A.

TABLE 4

Identification of Probe (AX4870) labeled Serine Hydrolases Present in 9005 Hydrolase A Butyl Sepharose HIC Pool

| Serine Hydrolase | Mw | Sequence |
| --- | --- | --- |
| Lysosomal Pro-X carboxypeptidase precursor (EC 3.4.16.2) (Prolyl | 55800 | -<br>.TIPGAENQPVIAIGGS*YGGMLAAWFR.<br>- |

Example 14

Relative Activity of Native 7340 Hydrolase, 9005 Hydrolase A and 9005 Hydrolase B against Phosphonate Prodrug Substrates The relative activities of several ester hydrolase enzymes, including native 7340 hydrolase, 9005 hydrolase A and 9005 hydrolase B against several phosphonate prodrug substrates (structure activity relationship, SAR) are determined. The SAR of 9005 hydrolase B against phosphonate prodrugs is distinct from the SAR observed for other ester hydrolases, including both 9005 hydrolase A and 7340 hydrolase.

Example 15

Specific Activity of Native 7340 Hydrolase and 9005 Hydrolase A with Phosphonate Prodrug Substrates The specific activities of several ester hydrolase enzymes, including native 7340 hydrolase and 9005 hydrolase A against various phosphonate prodrug substrates (structure activity relationship, SAR) are determined.

Example 16

Characterization of Exemplary Anti-HIV Compounds

HIV-1 Protease Enzyme Assay (Ki):

The assay is based on the fluorimetric detection of synthetic hexapeptide substrate cleavage by HIV-1 protease in a defined reaction buffer as initially described by Toth and Marshall, *Int. J Peptide Protein Res.* 36: 544 (1990).

The substrate used is (2-aminobenzoyl)Thr-Ile-Nle-(p-nitro)Phe-Gln-Arg substrate (Catalog No. H-2992) from Bachem California, Inc. (Torrance, Calif.). Recombinant HIV-1 protease expressed in *E. coli* is also obtained from Bachem California, Inc. (Torrance, Calif., Catalog No.

H9040). The reaction is conducted in a reaction buffer (RB) containing: 100 mM ammonium acetate, pH 5.3; 1 M sodium chloride; 1 mM ethylendiaminetetraacetic acid; 1 mM dithiothreitol (DTT); and 10% dimethylsulfoxide. In order to determine the inhibition constant (Ki), the following assay is conducted. A series of solutions containing identical amount of the enzyme (1 to 2.5 nM) and different concentrations of a tested inhibitor is prepared in the reaction buffer. The solutions are transferred (190 uL each) into a white 96-well plate. The reactions are preincubated for 15 minutes at 37° C. The substrate is solubilized in 100% dimethylsulfoxide at a concentration of 800 µM. The reaction is started by adding 10 µL of 800 µM substrate into each well to a final substrate concentration of 40 µM. The real-time reaction kinetics are measured at 37° C. by using a Gemini 96-well plate fluorimeter (Molecular Devices, Sunnyvale, Calif.) at λ(Ex)=330 nm and λ(Em)=420 nm. The initial velocities of the reactions are determined with different inhibitor concentrations. The Ki value (in picomolar concentration units) is calculated by using EnzFitter program (Biosoft, Cambridge, U.K.) according to an algorithm for tight-binding competitive inhibition described by Ermolieff et al., *Biochemistry* 36: 12364 (1997).

Anti-HIV-1 Cell Culture Assay ($EC_{50}$):

The following anti-HIV-1 assay is based on quantification of the HIV-1-associated cytopathic effect by a calorimetric detection of the viability of virus-infected cells in the presence or absence of tested inhibitors. The HIV-1-induced cell death is determined using a metabolic substrate 2,3-bis(2-methoxy-4-nitro-5-sulfophenyl)-2H-tetrazolium-5-carboxanilide (XTT), which substrate is converted only by intact cells into a product with specific absorption characteristics as described by Weislow et al., *J. Natl. Cancer Inst.* 81: 577 (1989).

In order to determine the $EC_{50}$, the following assay conditions are used. MT2 cells are maintained in RPMI-1640 medium supplemented with 5% fetal bovine serum and antibiotics. The MT2 cells are infected with the wild-type HIV-1 strain IIIB (Advanced Biotechnologies, Columbia, Md.) for 3 hours at 37° C. using the virus inoculum corresponding to a multiplicity of infection equal to 0.01. A set of solutions is prepared to contain various concentrations of the tested inhibitor by making 5-fold serial dilutions in 96-well plate (100 µL/well).

Infected cells are distributed into the 96-well plate (20,000 cells in 100 µL/well). Samples with untreated infected and untreated mock-infected control cells are included. The cells are incubated for 5 days at 37° C. 6 mL of XTT solution per assay plate is prepared at a concentration of 2 mg/mL in a phosphate-buffered saline, pH 7.4. The solution is heated in water-bath for 5 min at 55° C. 50 µL of N-methylphenazonium methasulfate (5 µg/mL) per 6 mL of XTT solution is added. 100 µL media is removed from each well on the assay plate. 100 µL of the XTT substrate solution is added to each well and the assay plate is incubated at 37° C. for 45 to 60 min in a $CO_2$ incubator. In order to inactivate the virus, 20 µL of 2% Triton X-100 is added to each well.

Absorbance is read at 450 nm and the background absorbance at 650 nm is subtracted. The percentage absorbance is plotted relative to untreated control and the $EC_{50}$ value is estimated as drug concentration resulting in a 50% protection of the infected cells.

Cytotoxicity Cell Culture Assay ($CC_{50}$):

The following cytotoxicity assay is based on the evaluation of cytotoxic effect of tested compounds using a metabolic substrate 2,3-bis(2-methoxy-4-nitro-5-sulfophenyl)-2H-tetrazolium-5-carboxanilide (XTT) as described by Weislow et al., *J. Natl. Cancer Inst.* 81: 577 (1989). MT2 cells are maintained in RPMI-1640 medium supplemented with 5% fetal bovine serum and antibiotics. A set of solutions is prepared to contain various concentrations of the tested inhibitor by making 5-fold serial dilutions in 96-well plate (100 µL/well). Cells are distributed into the 96-well plate (20,000 cells in 100 µL/well). Samples with untreated cells are included as a control. Cells are incubated for 5 days at 37° C. Sufficient XTT solution for 6 mL solution per assay plate is prepared in the dark at a concentration of 2mg/mL in a phosphate-buffered saline, pH 7.4. The solution is heated in a water-bath at 55° C. for 5 min. 50 µL of N-methylphenazonium methasulfate (5 µg/mL) is added per 6 mL of XTT solution. 100 µL media is removed from each well on the assay plate and 100 µL of the XTT substrate solution is added to each well. The assay plate is incubated at 37° C. for 45 to 60 min in a $CO_2$ incubator. 20 µL of 2% Triton X-100 is added to each well to stop the metabolic conversion of XTT. The absorbance at 450 nm is read and the background at 650 nm is subtracted. The absorbance is considered as directly proportional to the cell growth. The percentage absorbance relative to untreated control is plotted and the $CC_{50}$ value is estimated as drug concentration resulting in a 50% inhibition of the cell growth.

Resistance Evaluation (I50V and I84V/L90M Fold Change):

The assay is based on the determination of a difference in the susceptibility to a particular HIV protease inhibitor between the wild-type HIV-1 strain and a mutant HIV-1 strain containing specific drug resistance-associated mutation(s) in the viral protease gene. The absolute susceptibility of each virus ($EC_{50}$) to a particular tested compound is measured by using the XTT-based cytopathic assay as described above. The degree of resistance to a tested compound is calculated as fold difference in $EC_{50}$ between the wild type and a specific mutant virus. This represents a standard approach for HIV drug resistance evaluation as documented in various publications (e.g., Maguire et al., *Antimicrob. Agents Chemother*. 46: 731 (2002); Gong et al., *Antimicrob. Agents Chemother*. 44: 2319 (2000); Vandamme and De Clercq, in *Antiviral Therapy* 243 (E. De Clercq, ed.), ASM Press, Washington, D.C. (2001)).

HIV-1 Strains Used for Resistance Evaluation:

Two strains of mutant viruses containing I50V mutation in the protease gene are used in the resistance assays: one with M46I/I47V/I50V mutations (designated I50V #1) and the other with L01I/M46I/I50V (designated I50V #2) mutations in the viral protease gene. A third virus with I84V/L90M mutations is also employed in the resistance assays. Mutants I50V #1 and I84V/L90M are constructed by a homologous recombination between three overlapping DNA fragments: 1. linearized plasmid containing wild-type HIV-1 proviral DNA (strain HXB2D) with the protease and reverse transcriptase genes deleted; 2. DNA fragment generated by PCR amplification containing reverse transcriptase gene from HXB2D strain (wild-type); 3. DNA fragment of mutated viral protease gene that has been generated by PCR amplification. An approach similar to that described by Shi and Mellors, in *Antimicrob. Agents Chemother*. 41: 2781-85 (1997) is used for the construction of mutant viruses from the generated DNA fragments. Mixture of DNA fragments is delivered into Sup-T1 cells by using a standard electroporation technique. The cells are cultured in RPMI-1640 medium supplemented with 10% fetal bovine serum and antibiotics until the recombinant virus emerges (usually 10 to 15 days following the electroporation). Cell culture supernatant containing the recombinant virus is harvested and stored in aliquots. After verification of protease gene sequence and determination of the infectious virus titer, the viral stock is used for drug resistance studies. Mutant I50V #2 is an amprenavir-resistant HIV-1 strain selected in vitro from the wild-type IIIB strain in the presence of increasing concentration of amprenavir over a period of >9 months using an approach similar to that described by Partaledis et al., *J. Virol*. 69: 5228-5235 (1995). Virus capable of growing in the presence of 5 μM amprenavir is harvested from the supernatant of infected cells and used for resistance assays following the titration and protease gene sequencing.

All publications and patent applications cited are herein incorporated by reference in their entireties. Although certain embodiments are described in detail, one of ordinary skill in the art will clearly understand that many modifications are possible without departing from the spirit and scope of the teachings herein. All such modifications are intended to be encompassed within the present invention.

What is claimed is:

1. A method for identifying a candidate compound as a suitable prodrug, comprising:
   (a) providing a candidate compound having an esterified phosphonate group or an esterified carboxyl group;
   (b) contacting the candidate compound with an extract that comprises GS-9005 ester hydrolase A to produce one or more metabolite compounds; and
   (c) identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

2. The method of claim 1, wherein said extract is obtained from peripheral blood mononuclear cells.

3. The method of claim 1, wherein said extract is a fully purified extract.

4. The method of claim 1, wherein said extract comprises an enzyme comprising SEQ ID NO: 1 or SEQ ID NO: 2 or a fragment of either.

5. The method of claim 1, wherein said extract that comprises GS-9005 ester hydrolase A comprises prolylcarboxypeptidase.

6. The method of claim 1, wherein said providing step comprises providing a candidate compound formed by substituting a prototype compound with an esterified phosphonate group or an esterified carboxyl group.

7. The method of claim 1, further comprising (d) determining the intracellular persistence of the candidate compound.

8. The method of claim 1, further comprising (d) determining the intracellular persistence of at least one of the one or more metabolite compounds.

9. The method of claim 1, further comprising (d) determining the tissue selectivity of the candidate compound.

10. The method of claim 1, further comprising (d) determining the tissue selectivity of at least one of the one or more metabolite compounds.

11. A method for identifying a candidate compound as a suitable prodrug, comprising:
(a) providing a candidate compound formed by substituting a prototype compound believed to have therapeutic activity with an esterified phosphonate or an esterified carboxyl group;
(b) contacting the candidate compound with an extract of peripheral blood mononuclear cells that comprises GS-9005 ester hydrolase A to produce one or more metabolite compounds; and
(c) identifying the candidate compound as a suitable prodrug if at least one of the one or more metabolite compounds has a phosphonic acid group instead of the esterified phosphonate group of the candidate compound, or a carboxylic acid group instead of the esterified carboxyl group of the candidate compound.

12. The method of claim 11, wherein said extract of peripheral blood mononuclear cells comprises an enzyme comprising SEQ ID NO: 1 or SEQ ID NO: 2 or a fragment of either.

13. The method of claim 11, wherein said contacting step comprises contacting the candidate compound with the extract in a cell-free environment.

14. The method of claim 11, wherein said contacting step comprises contacting the candidate compound with the extract in vitro.

15. The method of claim 11, wherein said contacting step comprises contacting the candidate compound with the extract in cell culture.

16. The method of claim 11, wherein said contacting step comprises contacting the candidate compound with the extract in a culture of peripheral blood mononuclear cells.

17. The method of claim 11, wherein said therapeutic activity is therapeutic activity against HIV.

* * * * *

SEQUENCE LISTING

```
<160> NUMBER OF SEQ ID NOS: 2

<210> SEQ ID NO 1
<211> LENGTH: 496
<212> TYPE: PRT
<213> ORGANISM: Homo sapiens

<400> SEQUENCE: 1

Met Gly Arg Arg Ala Leu Leu Leu Leu Leu Leu Ser Phe Leu Ala Pro
1               5                   10                  15

Trp Ala Thr Ile Ala Leu Arg Pro Ala Leu Arg Ala Leu Gly Ser Leu
            20                  25                  30

His Leu Pro Thr Asn Pro Thr Ser Leu Pro Ala Val Ala Lys Asn Tyr
        35                  40                  45

Ser Val Leu Tyr Phe Gln Gln Lys Val Asp His Phe Gly Phe Asn Thr
    50                  55                  60

Val Lys Thr Phe Asn Gln Arg Tyr Leu Val Ala Asp Lys Tyr Trp Lys
65                  70                  75                  80

Lys Asn Gly Gly Ser Ile Leu Phe Tyr Thr Gly Asn Glu Gly Asp Ile
                85                  90                  95

Ile Trp Phe Cys Asn Asn Thr Gly Phe Met Trp Asp Val Ala Glu Glu
            100                 105                 110

Leu Lys Ala Met Leu Val Phe Ala Glu His Arg Tyr Tyr Gly Glu Ser
        115                 120                 125

Leu Pro Phe Gly Asp Asn Ser Phe Lys Asp Ser Arg His Leu Asn Phe
    130                 135                 140

Leu Thr Ser Glu Gln Ala Leu Ala Asp Phe Ala Glu Leu Ile Lys His
145                 150                 155                 160

Leu Lys Arg Thr Ile Pro Gly Ala Glu Asn Gln Pro Val Ile Ala Ile
                165                 170                 175

Gly Gly Ser Tyr Gly Gly Met Leu Ala Ala Trp Phe Arg Met Lys Tyr
            180                 185                 190

Pro His Met Val Val Gly Ala Leu Ala Ala Ser Ala Pro Ile Trp Gln
        195                 200                 205

Phe Glu Asp Leu Val Pro Cys Gly Val Phe Met Lys Ile Val Thr Thr
    210                 215                 220

Asp Phe Arg Lys Ser Gly Pro His Cys Ser Glu Ser Ile His Arg Ser
225                 230                 235                 240

Trp Asp Ala Ile Asn Arg Leu Ser Asn Thr Gly Ser Gly Leu Gln Trp
                245                 250                 255

Leu Thr Gly Ala Leu His Leu Cys Ser Pro Leu Thr Ser Gln Asp Ile
            260                 265                 270

Gln His Leu Lys Asp Trp Ile Ser Glu Thr Trp Val Asn Leu Ala Met
        275                 280                 285

Val Asp Tyr Pro Tyr Ala Ser Asn Phe Leu Gln Pro Leu Pro Ala Trp
    290                 295                 300

Pro Ile Lys Val Val Cys Gln Tyr Leu Lys Asn Pro Asn Val Ser Asp
```

-continued

```
            305                 310                 315                 320
Ser Leu Leu Leu Gln Asn Ile Phe Gln Ala Leu Asn Val Tyr Tyr Asn
                325                 330                 335

Tyr Ser Gly Gln Val Lys Cys Leu Asn Ile Ser Glu Thr Ala Thr Ser
            340                 345                 350

Ser Leu Gly Thr Leu Gly Trp Ser Tyr Gln Ala Cys Thr Glu Val Val
            355                 360                 365

Met Pro Phe Cys Thr Asn Gly Val Asp Asp Met Phe Glu Pro His Ser
        370                 375                 380

Trp Asn Leu Lys Glu Leu Ser Asp Asp Cys Phe Gln Gln Trp Gly Val
385                 390                 395                 400

Arg Pro Arg Pro Ser Trp Ile Thr Thr Met Tyr Gly Gly Lys Asn Ile
                405                 410                 415

Ser Ser His Thr Asn Ile Val Phe Ser Asn Gly Glu Leu Asp Pro Trp
            420                 425                 430

Ser Gly Gly Gly Val Thr Lys Asp Ile Thr Asp Thr Leu Val Ala Val
            435                 440                 445

Thr Ile Ser Glu Gly Ala His His Leu Asp Leu Arg Thr Lys Asn Ala
        450                 455                 460

Leu Asp Pro Met Ser Val Leu Leu Ala Arg Ser Leu Glu Val Arg His
465                 470                 475                 480

Met Lys Asn Trp Ile Arg Asp Phe Tyr Asp Ser Ala Gly Lys Gln His
                485                 490                 495

<210> SEQ ID NO 2
<211> LENGTH: 475
<212> TYPE: PRT
<213> ORGANISM: Homo sapiens

<400> SEQUENCE: 2

Leu Arg Pro Ala Leu Arg Ala Leu Gly Ser Leu His Leu Pro Thr Asn
1               5                   10                  15

Pro Thr Ser Leu Pro Ala Val Ala Lys Asn Tyr Ser Val Leu Tyr Phe
                20                  25                  30

Gln Gln Lys Val Asp His Phe Gly Phe Asn Thr Val Lys Thr Phe Asn
            35                  40                  45

Gln Arg Tyr Leu Val Ala Asp Lys Tyr Trp Lys Lys Asn Gly Gly Ser
        50                  55                  60

Ile Leu Phe Tyr Thr Gly Asn Glu Gly Asp Ile Ile Trp Phe Cys Asn
65                  70                  75                  80

Asn Thr Gly Phe Met Trp Asp Val Ala Glu Glu Leu Lys Ala Met Leu
                85                  90                  95

Val Phe Ala Glu His Arg Tyr Tyr Gly Glu Ser Leu Pro Phe Gly Asp
            100                 105                 110

Asn Ser Phe Lys Asp Ser Arg His Leu Asn Phe Leu Thr Ser Glu Gln
        115                 120                 125

Ala Leu Ala Asp Phe Ala Glu Leu Ile Lys His Leu Lys Arg Thr Ile
    130                 135                 140

Pro Gly Ala Glu Asn Gln Pro Val Ile Ala Ile Gly Gly Ser Tyr Gly
145                 150                 155                 160

Gly Met Leu Ala Ala Trp Phe Arg Met Lys Tyr Pro His Met Val Val
                165                 170                 175

Gly Ala Leu Ala Ala Ser Ala Pro Ile Trp Gln Phe Glu Asp Leu Val
            180                 185                 190
```

-continued

```
Pro Cys Gly Val Phe Met Lys Ile Val Thr Thr Asp Phe Arg Lys Ser
        195                 200                 205
Gly Pro His Cys Ser Glu Ser Ile His Arg Ser Trp Asp Ala Ile Asn
    210                 215                 220
Arg Leu Ser Asn Thr Gly Ser Gly Leu Gln Trp Leu Thr Gly Ala Leu
225                 230                 235                 240
His Leu Cys Ser Pro Leu Thr Ser Gln Asp Ile Gln His Leu Lys Asp
                245                 250                 255
Trp Ile Ser Glu Thr Trp Val Asn Leu Ala Met Val Asp Tyr Pro Tyr
            260                 265                 270
Ala Ser Asn Phe Leu Gln Pro Leu Pro Ala Trp Pro Ile Lys Val Val
        275                 280                 285
Cys Gln Tyr Leu Lys Asn Pro Asn Val Ser Asp Ser Leu Leu Leu Gln
    290                 295                 300
Asn Ile Phe Gln Ala Leu Asn Val Tyr Tyr Asn Tyr Ser Gly Gln Val
305                 310                 315                 320
Lys Cys Leu Asn Ile Ser Glu Thr Ala Thr Ser Ser Leu Gly Thr Leu
                325                 330                 335
Gly Trp Ser Tyr Gln Ala Cys Thr Glu Val Val Met Pro Phe Cys Thr
            340                 345                 350
Asn Gly Val Asp Asp Met Phe Glu Pro His Ser Trp Asn Leu Lys Glu
        355                 360                 365
Leu Ser Asp Asp Cys Phe Gln Gln Trp Gly Val Arg Pro Arg Pro Ser
    370                 375                 380
Trp Ile Thr Thr Met Tyr Gly Gly Lys Asn Ile Ser Ser His Thr Asn
385                 390                 395                 400
Ile Val Phe Ser Asn Gly Glu Leu Asp Pro Trp Ser Gly Gly Gly Val
                405                 410                 415
Thr Lys Asp Ile Thr Asp Thr Leu Val Ala Val Thr Ile Ser Glu Gly
            420                 425                 430
Ala His His Leu Asp Leu Arg Thr Lys Asn Ala Leu Asp Pro Met Ser
        435                 440                 445
Val Leu Leu Ala Arg Ser Leu Glu Val Arg His Met Lys Asn Trp Ile
    450                 455                 460
Arg Asp Phe Tyr Asp Ser Ala Gly Lys Gln His
465                 470                 475
```